United States Patent
Cuccui et al.

(10) Patent No.: US 11,179,454 B2
(45) Date of Patent: Nov. 23, 2021

(54) WHOLE CELL VACCINES

(71) Applicant: London School of Hygiene and Tropical Medicine, London (GB)

(72) Inventors: Jon Cuccui, London (GB); Brendan Wren, London (GB); Alexandra Faulds-Pain, London (GB)

(73) Assignee: London School of Hygiene and Tropical Medicine, London (GB)

( * ) Notice: Subject to any disclaimer, the term of this patent is extended or adjusted under 35 U.S.C. 154(b) by 0 days.

(21) Appl. No.: 16/493,638

(22) PCT Filed: Mar. 14, 2018

(86) PCT No.: PCT/GB2018/050650
§ 371 (c)(1),
(2) Date: Sep. 12, 2019

(87) PCT Pub. No.: WO2018/167485
PCT Pub. Date: Sep. 20, 2018

(65) Prior Publication Data
US 2020/0009241 A1      Jan. 9, 2020

(30) Foreign Application Priority Data

Mar. 15, 2017 (GB) ..................... 1704103
Mar. 15, 2017 (GB) ..................... 1704108

(51) Int. Cl.
| | | |
|---|---|---|
| *A61K 39/02* | (2006.01) | |
| *A61K 39/104* | (2006.01) | |
| *A61P 31/04* | (2006.01) | |
| *A61K 39/116* | (2006.01) | |
| *A61K 39/00* | (2006.01) | |

(52) U.S. Cl.
CPC .......... *A61K 39/104* (2013.01); *A61K 39/105* (2013.01); *A61K 39/116* (2013.01); *A61P 31/04* (2018.01); *A61K 2039/6068* (2013.01)

(58) Field of Classification Search
None
See application file for complete search history.

(56) References Cited

U.S. PATENT DOCUMENTS

2014/0004144 A1    1/2014    Bey et al.

FOREIGN PATENT DOCUMENTS

| CN | 103 343 102 A | 10/2013 |
|---|---|---|
| WO | WO 2009/104074 A2 | 8/2009 |
| WO | WO 2010/108682 A1 | 9/2010 |
| WO | WO 2011/027116 A1 | 3/2011 |
| WO | WO 2012/034077 A2 | 3/2012 |
| WO | WO 2013/043643 A1 | 3/2013 |
| WO | WO 2014/111724 A1 | 7/2014 |
| WO | WO 2014/114926 A1 | 7/2014 |

OTHER PUBLICATIONS

Liang et al (Scientific Reports. Aug. 2016. 6:30966; pp. 1-12).*
Accession No. NLM21604553, Weishengwu Xuebao (publisher), 2011.
Cuccui et al., "Exploitation of bacterial N-linked glycosylation to develop a novel recombinant glycoconjugate vaccine against Francisella tularensis," Open Biol. 3:130002, 2013.
Jervis et al., "Characterization of the Structurally Diverse N-Linked Glycans of Campylobacter Species," J Bacteriol. 194:2355-2362, 2012.
Kock et al., "Intranasal immunization with a live Streptococcus suis isogenic ofs mutant elicited suilysin-neutralization titers but failed to induce opsonizing antibodies and protection," Vet Immunol Immunopathol. 132:135-145, 2009.
Terra et al., "Recent developments in bacterial protein glycan coupling technology and glycoconjugate vaccine design," J Med Microbiol. 61:919-926, 2012.
Vanier et al., "Disruption of srtA gene in Streptococcus suis results in decreased interactions with endothelial cells and extracellular matrix proteins," Vet Microbiol. 127:417-424, 2008.
Wang et al., "The involvement of sortase A in high virulence of STSS-causing Streptococcus suis serotype 2," Arch Microbiol. 191:23-33, 2009.
Wang et al., "Construction of a Streptococcus iniae sortase A mutant and evaluation of its potential as an attenuated modified live vaccine in Nile tilapia (Oreochromis niloticus)," Fish & Shellfish Immunol. 40:392-398, 2014.
Combined Search and Examination Report dated Dec. 19, 2016 for GB 1603958.8 (9 pages).
Combined Search and Examination Report dated Dec. 19, 2016 for GB 1603963.8 (11 pages).
International Search Report and Written Opinion dated Jun. 28, 2018 for International Application No. PCT/GB2018/050650 (10 pages).

* cited by examiner

*Primary Examiner* — Jennifer E Graser
(74) *Attorney, Agent, or Firm* — Klarquist Sparkman, LLP

(57) ABSTRACT

The disclosure relates to attenuated bacterial cells expressing glycans and glycoconjugate antigens and their use in the manufacture of whole cell vaccines effective at preventing or treating bacterial infections in non-human species.

10 Claims, 7 Drawing Sheets

Specification includes a Sequence Listing.

```
Contig     ████████████████████████████████████████████  (SEQ ID NO: 63)
Expected   ------------------------AIGGCGTCAAATTTTAATTTCGCTAAA  (SEQ ID NO: 64)
                                   ***************************

Contig     ████████████████GATTATCGCC██████████████████  (SEQ ID NO: 65)
Expected   ----------------------------------ATGGCGTCAAATTTTAATTTCGCTAAA  (SEQ ID NO: 64)
```

Figure 8A
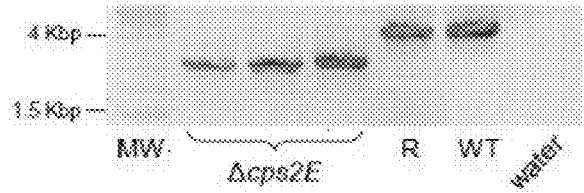
Figure 8B
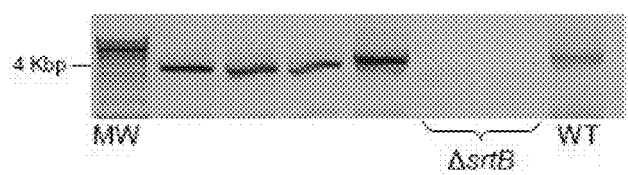
Figure 8C
Figure 9
```
Contig    atttcacacaggaaacaGAATTCATGGCGTCAAATTTTAATTTCGCTAAA  (SEQ ID NO: 63)
Expected  ----------------------ATGGCGTCAAATTTTAATTTCGCTAAA  (SEQ ID NO: 64)
                                ********************************
Contig    atttcacacaggaaacaGAATTCGATTATCGCCATGGCGTCAAATTTTAATTTCGCTAAA  (SEQ ID NO: 65)
Expected  --------------------------------ATGGCGTCAAATTTTAATTTCGCTAAA  (SEQ ID NO: 64)
                                           ***************************
```
Figure 10
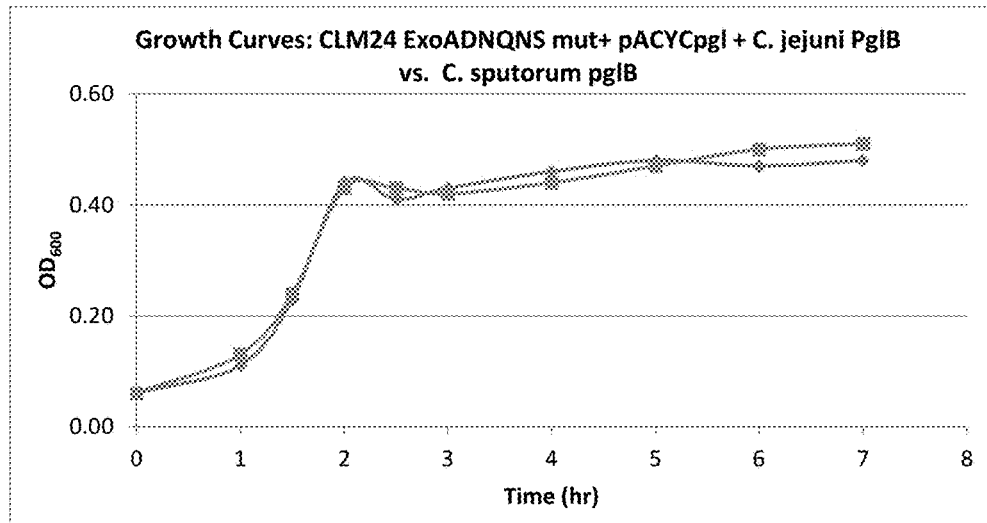

WHOLE CELL VACCINES

CROSS REFERENCE TO RELATED APPLICATIONS

This is the U.S. National Stage of International Application No. PCT/GB2018/050650, filed Mar. 14, 2018, which was published in English under PCT Article 21(2), which in turn claims the benefit of Great Britain Application No. 1704108.8, filed Mar. 15, 2017 and Great Britain Application No. 1704103.9, filed Mar. 15, 2017.

FIELD OF THE INVENTION

The disclosure relates to attenuated bacterial cells expressing glycan and glycoconjugate antigens and their use in the manufacture of whole cell vaccines or immunogenic compositions effective at eliciting an immune response in non-human animal species and preventing or treating bacterial infections.

BACKGROUND TO THE INVENTION

Animal-health is facing new and additional challenges as a result of the growing demand of animal products. The confinement and housing of hundreds of animals such as swine, cattle or chickens although reducing the costs of growth and production of animals increases the incidence and spread of disease significantly. Animal diseases are not just associated with economic risks such as productivity losses, market disruption or livelihood risks for the farmer, but have also human health risk implications. The maintenance of healthy livestock is essential for economic and societal prosperity, however, the application and development of vaccines in veterinary medicine is rudimentary, mainly due to the necessity for reduced costs to vaccinate animals and because our knowledge of the pathogens that cause animal diseases is not as advanced as for those that infect humans. For example, glycoconjugate vaccines enjoy widespread use in humans; however, veterinary applications are limited due to their still high cost of development.

Pathogenic bacteria are a major cause of infectious diseases that affect animals. The control of bacterial infection in agriculturally important animal species is problematic due to the close proximity of animals to each other which can facilitate the dissemination of infection throughout a herd. Herd immunity exists when a larger proportion of animals are immune to a particular infectious agent but can be undermined once a significant number of non-immunized animals are present in the herd. To implement herd immunity it is necessary to continually monitor animals for susceptible members of the herd to control transmission. The control of bacterial transmission is by a number of measures which are labour intensive and expensive to implement and include, quarantine; elimination of the animal reservoir of infection; environmental control [i.e. maintenance of clean water and food supply, hygienic disposal of excrement, air sanitation]; use of antibiotics; use of probiotics to enhance the growth of non-pathogenic bacteria and inhibit the growth of pathogenic bacteria and active immunization to increase the number of resistant members of a herd.

The production of herds that are generally resistant to bacterial infection requires the identification of antigens that form the basis of vaccines which induce immunity.

Furthermore, animal species harbour bacterial pathogens that also infect humans. A zoonosis is an infectious disease transmittable from a non-human animal to a human. Examples of zoonotic bacterial infections caused by Gram negative bacteria include brucellosis caused by *Brucella* spp which is transmitted to humans from infected milk and meat; campylobacteriosis caused by *Campylobacter* spp; cholera caused by *Vibrio cholera*; yersinosis caused by *Yersina* spp from infected uncooked meat or unpasteurized milk; and salmonellosis caused by *Salmonella* spp from infected meat, in particular pork and eggs. There are various diseases which can affect livestock caused by a wide range of bacteria such as colibacillosis in chicken, mastitis in dairy cattle or respiratory diseases in pigs. Once infection occurs, treatment options are limited, often dependent on antibiotics which are costly and more importantly their repeated use contributes to the development of resistance. Protective vaccinations are therefore the preferred method, preventing and contributing in general to the eradication of non-human animal disease.

A defining characteristic of a successful vaccine is the ability to evoke long-lasting protective immune response with minimal side effects. Most veterinary vaccines are either based on live attenuated bacterial strains or products containing no live components of the antigen, such as inactivated whole-cell vaccines or subunit vaccines containing only the antigenic parts of the pathogen based on protein or carbohydrate subunits, recombinant proteins, peptides or nucleic acid-based products.

Glycoconjugate vaccines comprising carbohydrate-specific antigens can provide protection against a variety of pathogenic bacteria. However, glycoconjugate vaccines often suffer from low immunogenicity and fail to generate a sufficient memory B-lymphocyte cell response. The coupling of a polysaccharide antigen to a protein carrier, generating a glycoconjugate increases immunogenicity significantly. Currently licensed human glycoconjugate vaccines include those against *Haemophilus influenzae, Neisserria meningitidis* and *Streptococcus pneumoniae*, which comprise bacterial polysaccharides chemically bound to carrier proteins. The *H. influenzae* type B (Hib) vaccine or Prevnar®, a 13-valent capsule-based glycoconjugate vaccine protective against diseases caused by *S. pneumonia*, uses the carrier protein iCRM197, a non-toxic version of diphtheria toxin isolated from *Corynebacterium diphtheria*.

These glycoconjugate vaccines are effective but their production requires both the purification of polysaccharide glycan from the native pathogen and the chemical coupling of the polysaccharide to a suitable protein carrier which is a highly costly, inefficient and time-consuming process. The glycan is either obtained from a bacterial source or by chemical synthesis. Carrier proteins are typically bacterial toxins such as tetanus and diphtheria (most commonly as the recombinant form, CRM197), although other carriers have been used. For example, keyhole limpet hemocyanin (KLH) has often been used in animal vaccine studies. The coupling of glycans to the carrier protein requires chemical activation of the glycan and/or carrier which generally takes several steps and results in heterogeneous products.

The use of modified bacterial strains comprising an oligosaccharyltransferase enabling the transfer of an antigenic polysaccharide glycan onto a protein carrier offer an economical alternative for the production of glycoconjugates and are known in the art. Production of glycoconjugate vaccines for human use in a bacterial expression system are disclosed in WO2009/104074 or WO2014/114926. The production of glycoconjugates in a bacterial expression system requires the co-expression of three genes: an acceptor protein, a polysaccharide biosynthetic locus and, for the coupling reaction, an oligosaccharyltransferase enzyme. Co-expression in just one host leads however often to suboptimal yields, which makes it commercial not viable.

This disclosure uses glycan coupling technology to express antigenic polysaccharides of one or more pathogenic bacteria in live attenuated whole cell vaccines by introducing transcription cassettes encoding the antigenic polysaccharide, oligosaccharyltransferase and acceptor proteins either as part of a plasmid or inserted directly into the genome, thus increasing their protective spectrum against multiple pathogens. Moreover, recombinant expression systems with decreased translational efficiency comprising oligosaccharyltransferases, toxic carrier proteins or genes encoding proteins required for glycan biosynthesis are also disclosed. Translational efficiency is decreased by providing a vector with increased distance between the ribosome binding site [RBS] and the translational start codon thus enabling bacterial growth to a high density and avoiding deleterious effects of expressing recombinant proteins at concentrations which are toxic to the bacterial cell.

STATEMENT OF THE INVENTION

According to an aspect of the invention there is provided a pathogenic bacterial cell wherein said cell is transformed with a transcription cassette comprising a biosynthetic locus comprising one or more polypeptides required for the synthesis of a heterologous glycan antigen not expressed by said transformed pathogenic bacterial cell wherein said heterologous glycan antigen is expressed at the bacterial cell surface.

According to an aspect of the invention there is provided a pathogenic bacterial cell wherein said cell is transformed with one or more transcription cassettes comprising:
  a nucleic acid molecule encoding a oligosaccharyltransferase polypeptide,
  a nucleic acid molecule encoding one or more carrier polypeptides comprising at least one glycosylation site as a substrate for said oligosaccharyltransferase and a nucleic acid molecule encoding a biosynthetic locus comprising one or more polypeptides required for the synthesis of a heterologous glycan antigen not expressed by said transformed pathogenic bacterial cell characterised in that said pathogenic bacterial cell is attenuated and said heterologous glycan antigen is expressed at the bacterial cell surface and wherein said heterologous glycan is also coupled to said carrier polypeptide to provide a glycoconjugate retained within said attenuated pathogenic bacterial cell.

In a further preferred embodiment of the invention said bacterial cell comprises at least one inactive or mutated gene encoding a membrane polypeptide or membrane associated polypeptide wherein the live pathogenic bacterial cell is attenuated and the attenuation is the result of said gene inactivation or mutation.

In a preferred embodiment of the invention at least 2, 3 or more genes are inactive or mutated.

In a preferred embodiment of the invention said gene is selected from the group consisting of: a gene encoding a sortase and/or a gene encoding a polysaccharide modification enzyme wherein said modification is associated with the inactivation or inhibition of expression of said sortase or polysaccharide modification gene.

In a preferred embodiment of the invention the gene encoding said sortase is encoded by a nucleotide sequence selected from the group consisting of:
  i) a nucleic acid molecule comprising a nucleotide sequence as set forth in SEQ ID NO: 1;
  ii) a nucleic acid molecule comprising a nucleotide sequence wherein said sequence is degenerate as a result of the genetic code to the nucleotide sequence defined in (i); and
  iii) a nucleic acid molecule the complementary strand of which hybridizes under stringent hybridization conditions to the nucleotide sequence in i) and ii) above wherein said nucleic acid molecule encodes a sortase.

In a preferred embodiment of the invention the gene encoding said sortase is encoded by a nucleotide sequence selected from the group consisting of:
  i) a nucleic acid molecule comprising a nucleotide sequence as set forth in SEQ ID NO: 2;
  ii) a nucleic acid molecule comprising a nucleotide sequence wherein said sequence is degenerate as a result of the genetic code to the nucleotide sequence defined in (i); and
  iii) a nucleic acid molecule the complementary strand of which hybridizes under stringent hybridization conditions to the nucleotide sequence in i) and ii) above wherein said nucleic acid molecule encodes a sortase.

In a preferred embodiment of the invention the gene encoding said polysaccharide modification enzyme is encoded by a nucleotide sequence selected from the group consisting of:
  i) a nucleic acid molecule comprising a nucleotide sequence as set forth in SEQ ID NO: 3;
  ii) a nucleic acid molecule comprising a nucleotide sequence wherein said sequence is degenerate as a result of the genetic code to the nucleotide sequence defined in (i); and
  iii) a nucleic acid molecule the complementary strand of which hybridizes under stringent hybridization conditions to the nucleotide sequence in i) and ii) above wherein said nucleic acid molecule encodes a polysaccharide modification enzyme.

Hybridization of a nucleic acid molecule occurs when two complementary nucleic acid molecules undergo an amount of hydrogen bonding to each other. The stringency of hybridization can vary according to the environmental conditions surrounding the nucleic acids, the nature of the hybridization method, and the composition and length of the nucleic acid molecules used. Calculations regarding hybridization conditions required for attaining particular degrees of stringency are discussed in Sambrook et al., Molecular Cloning: A Laboratory Manual (Cold Spring Harbor Laboratory Press, Cold Spring Harbor, N.Y., 2001); and Tijssen, Laboratory Techniques in Biochemistry and Molecular Biology—Hybridization with Nucleic Acid Probes Part I, Chapter 2 (Elsevier, New York, 1993). The $T_m$ is the temperature at which 50% of a given strand of a nucleic acid molecule is hybridized to its complementary strand. The following is an exemplary set of hybridization conditions and is not limiting:

Very High Stringency (Allows Sequences that Share at Least 90% Identity to Hybridize)
  Hybridization: 5× SSC at 65° C. for 16 hours
  Wash twice: 2× SSC at room temperature (RT) for 15 minutes each
  Wash twice: 0.5× SSC at 65° C. for 20 minutes each
High Stringency (Allows Sequences that Share at Least 80% Identity to Hybridize)
  Hybridization: 5×-6× SSC at 65° C.-70° C. for 16-20 hours
  Wash twice: 2× SSC at RT for 5-20 minutes each
  Wash twice: 1× SSC at 55° C.-70° C. for 30 minutes each Low Stringency (Allows Sequences that Share at Least 50% Identity to Hybridize)
  Hybridization: 6× SSC at RT to 55° C. for 16-20 hours
  Wash at least twice: 2×-3× SSC at RT to 55° C. for 20-30 minutes each.

In a preferred embodiment of the invention sequences share at least 50%, 55%, 60%, 65%, 70%, 75%, 80%, 90%, 95%, 96%, 97%, 98% or 99% sequence identity over the full length sequence set forth in SEQ ID NO: 1, 2 or 3.

In a preferred embodiment of the invention said gene encoding the sortase and/or said polysaccharide modification enzyme is modified by deletion of all or part of the nucleotide sequence encoding said sortase and/or polysaccharide modification enzyme, or all or part of a regulatory region controlling expression of said sortase and/or polysaccharide modification enzyme.

"Attenuated", in the context of the present disclosure, means a modified bacterial cell the virulence of which has been reduced or weakened but still capable of provoking an immune response, for example a humoral or cellular response, in a subject animal that has been administered a composition comprising the attenuated bacterial cell. Attenuated bacterial cells according to the invention may be inactivated.

The attenuated bacterial cell according to the invention is transformed to provide a cell that provokes an immune response to multiple foreign antigens. An animal subject raises an immune response to antigens native to the attenuated bacterial cell. This is supplemented by a response to the foreign heterogeneous glycan expressed at the cell surface. The immune response by the animal includes raising opsonic antibodies that seek out and destroy cells expressing each glycan antigen. The destruction of the engineered bacterial cells results in the release glycoconjugate expressed and retained in the bacterial cell, for example glycoconjugate retained in the periplasmic space. This acts as a booster to further induce a second immune response directed to the glycoconjugate thereby providing a sustained exposure of antigen to the animal subject. The use of antigens derived from multiple bacterial pathogens allows protection against more than one bacterial pathogen.

In a further alternative preferred embodiment of the invention said attenuated pathogenic bacterial cell is a zoonotic bacterial species.

Animal species harbour bacterial pathogens that also infect humans. A zoonosis is an infectious disease transmittable from a non-human animal to a human. Examples of zoonotic bacterial infections caused by Gram negative bacteria include brucellosis caused by *Brucella* spp which is transmitted to humans from infected milk and meat; campylobacteriosis caused by *Campylobacter* spp; cholera caused by *Vibrio cholera*; yersinosis caused by *Yersinia* spp from infected uncooked meat or unpasteurized milk; and salmonellosis caused by *Salmonella* spp from infected meat, in particular pork and eggs.

In a preferred embodiment of the invention said oligosaccharyltransferase is a *Campylobacter* oligosaccharyltransferase.

In a preferred embodiment of the invention said *Campylobacter* oligosaccharyltransferase is a *Campylobacter jejuni* oligosaccharyltransferase.

In an alternative embodiment of the invention said *Campylobacter* oligosaccharyltransferase is a *Campylobacter sputorum* oligosaccharyltransferase.

In a preferred embodiment of the invention said oligosaccharyltransferase is encoded by a nucleic acid molecule comprising the nucleotide sequence as set forth in SEQ ID NO: 4, or a nucleotide sequence that has at least 50% nucleotide sequence identity over the full length nucleotide sequence set forth in SEQ ID NO: 4.

In a preferred embodiment of the invention said oligosaccharyltransferase is encoded by a nucleic acid molecule comprising the nucleotide sequence as set forth in SEQ ID NO: 5 or 6 or a nucleotide sequence that has at least 50% nucleotide sequence identity over the full length nucleotide sequence set forth in SEQ ID NO: 5 or 6.

In a preferred embodiment of the invention said oligosaccharyltransferase is represented by the amino acid sequence set forth in SEQ ID NO: 7, or an amino acid sequence that is at least 50% identical to the full length amino acid sequence set forth in SEQ ID NO: 7.

In a preferred embodiment of the invention said oligosaccharyltransferase is represented by the amino acid sequence set forth in SEQ ID NO: 8, or an amino acid sequence that is at least 50% identical to the full length amino acid sequence set forth in SEQ ID NO: 8.

In a preferred embodiment, the oligosaccharyltransferase has at least 55% identity, more preferably at least 60% identity, even more preferably at least 65% identity, still more preferably at least 70%, 71%, 72%, 73%, 74%, 75%, 76%, 77%, 78%, 79%, 80%, 85% or 90% identity. Most preferably at least 95%, 96%, 97%, 98% or 99% identity with the full length nucleotide sequence or amino acid sequence as set forth in SEQ ID NO: 4, 5, 6, 7 or 8

In a preferred embodiment of the invention said carrier polypeptide comprises the amino acid motif: Asn-X-Ser or Asn-X-Thr where X is any amino acid except proline.

In an alternative embodiment of the invention said acceptor polypeptide includes the amino acid motif: D/E-X-N-X-S/T (SEQ ID NO: 62), wherein X is any amino acid except proline.

In an alternative preferred embodiment of the invention said acceptor polypeptide includes a glycosylation motif selected from the group consisting of: DQNAT (SEQ ID NO 44), DNNNT (SEQ ID NO 45), DNNNS (SEQ ID NO 46), DQNRT (SEQ ID NO 47), ENNFT (SEQ ID NO 48), DSNST (SEQ ID NO 49), DQNIS (SEQ ID NO 50), DQNVS (SEQ ID NO 51), DNNVS (SEQ ID NO 52), DYNVS (SEQ ID NO 53), DFNVS (SEQ ID NO 54), DFNAS (SEQ ID NO 55), DFNSS (SEQ ID NO 56), DVNAT (SEQ ID NO 57), DFNVT (SEQ ID NO 58), DVNAS (SEQ ID NO 59), DVNVT (SEQ ID NO 60), EVNAT (SEQ ID NO 61).

In a preferred embodiment of the invention said carrier polypeptide is an endogenous carrier polypeptide encoded by the genome of said attenuated pathogenic bacterial cell.

In an alternative embodiment of the invention said carrier polypeptide is a heterologous carrier polypeptide encoded by a nucleic acid molecule not naturally expressed by said attenuated pathogenic bacterial cell.

In a preferred embodiment of the invention said heterologous carrier polypeptide is encoded by a nucleic acid molecule isolated from a pathogenic bacterial species.

In a preferred embodiment of the invention said heterologous carrier polypeptide is encoded by a nucleotide sequence as set forth in SEQ ID NO: 9, 10 or 11.

In a preferred embodiment of the invention said nucleic acid molecule encoding a biosynthetic locus comprising one or more polypeptides required for the synthesis of a heterologous glycan antigen encodes a capsular polysaccharide.

In a preferred embodiment of the invention said polysaccharide is O-antigen.

O-antigens comprising repetitive glycan polymers are the polysaccharide component of lipopolysaccharides (LPS)

found associated with the outer membrane of gram negative bacteria. O-antigens typically elicit a strong immune response in animals. The composition of the O chain varies from bacterial strain to bacterial strain and there are over 160 different O antigen structures produced by different *E. coli* strains known. O-antigens are exposed on the outer surface of the bacterial cell, and serve a target for recognition by host antibodies. Examples of polysaccharide synthesis loci are well known in the art and can be found in: "Genetic analysis of the capsular biosynthetic locus from all 90 pneumococcal serotypes", Bentley S D, Aanensen D M, Mavroidi A, Saunders D, Rabbinowitsch E, Collins M, Donohoe K, Harris D, Murphy L, Quail M A, Samuel G, Skovsted I C, Kaltoft M S, Barrell B, Reeves P R, Parkhill J, Spratt B G. PLoS Genet. 2006 March: 2 (3):e31; "Gene content and diversity of the loci encoding biosynthesis of capsular polysaccharides of the 15 serovar reference strains of *Haemophilus parasuis*." Howell K J, Weinert L A, Luan S L, Peters S E, Chaudhuri R R, Harris D, Angen O, Aragon V, Parkhill J, Langford P R, Rycroft A N, Wren B W, Tucker A W, Maskell D J; BRaDP1T Consortium. J Bacteriol. 2013 September: 195(18):4264-73. doi: 10.1128/JB.00471-13. Epub 2013 Jul. 19; "Exploitation of bacterial N-linked glycosylation to develop a novel recombinant glycoconjugate vaccine against *Francisella tularensis*". Cuccui J, Thomas R M, Moule M G, D'Elia R V, Laws T R, Mills D C, Williamson D, Atkins T P, Prior J L, Wren B W. Open Biol. 2013 May 22; 3(5):130002; and "Characterization of the structurally diverse N-linked glycans of *Campylobacter* species". Jervis A J, Butler J A, Lawson A J, Langdon R, Wren B W, Linton D. J Bacteriol. 2012 May: 194(9):2355-62.

In an alternative preferred embodiment of the invention said polysaccharide is a heptasaccharide.

In a preferred embodiment of the invention said biosynthetic locus comprises a nucleic acid molecule comprising a nucleotide sequence as is set forth in SEQ ID NO: 12.

In a preferred embodiment of the invention said nucleic acid molecule encoding said oligosaccharyltransferase is stably integrated into the genome of said attenuated pathogenic bacterial cell.

In a further preferred embodiment of the invention said nucleic acid molecule encoding said carrier polypeptide is stably integrated into the genome of said attenuated pathogenic bacterial cell.

In a yet further preferred embodiment of the invention said nucleic acid molecule encoding said biosynthetic locus is stably integrated into the genome of said attenuated pathogenic bacterial cell.

Genetic transformation of an attenuated pathogenic bacterial cell according to the invention using a transcription cassette as herein disclosed can be via transformation using episomal vectors that are replicated separately from the genome of the attenuated pathogenic bacterial cell to provide multiple copies of a gene or genes. Alternatively, integrating vectors, for example a transposon, that recombine with the genome of the attenuated pathogenic bacterial cell and which is replicated with the genome of said attenuated pathogenic bacterial cell.

In a preferred embodiment of the invention said nucleic acid molecule encoding a oligosaccharyltransferase polypeptide, a carrier polypeptide and a biosynthetic locus comprising one or more polypeptides required for the synthesis of a heterogeneous glycan antigen are each integrated into the genome of said attenuated pathogenic bacterial cell.

In a preferred embodiment of the invention said transcription cassette comprises a promoter operably linked to at least the nucleic acid molecule encoding said oligosaccharyltransferase polypeptide.

In a preferred embodiment of the invention said transcription cassette comprises a promoter operably linked to at least the nucleic acid molecule encoding said carrier polypeptide In a preferred embodiment of the invention said one or more polypeptides required for the synthesis of a heterologous glycan antigen are operably linked to one or more promoters to provide expression of each or all nucleic acid molecules encoding said polypeptides.

In a preferred embodiment of the invention said promoter is further operably linked to a ribosome binding site wherein there is provided a nucleotide spacer sequence between the 3' prime end of said ribosome binding site and the 5' initiating start codon of the nucleic acid molecule encoding said carrier polypeptide and/or heterologous glycan antigen and/or oligosaccharyltransferase polypeptide wherein translation from the nucleic acid molecule encoding said carrier polypeptide and/or heterologous glycan antigen and/or oligosaccharyltransferase polypeptide is reduced when compared to a control nucleic acid molecule encoding said recombinant polypeptide that does not comprise said nucleotide spacer sequence.

Ribosome Binding Sites in prokaryotic nucleic acid molecules are referred as a Shine Dalgarno [SD] sequence and is a consensus sequence that is typically positioned 5-13 nucleotides upstream of an initiating codon of the nucleic acid molecule. The consensus RBS sequence consists of a purine rich region followed by an A and T-rich translational spacer region, for example the consensus AGGAGG or AGGAGGU. Initiating codons are commonly AUG but translation can also be initiated at codons such as GUG, UUG, AUU or CUG. In a preferred embodiment of the invention said nucleotide spacer sequence is at least 13 nucleotides in length.

In a preferred embodiment of the invention said nucleotide spacer sequence is 13 and 40 nucleotides in length; preferably the nucleotide spacer sequence is between 13 and 20 nucleotides in length.

In a preferred embodiment of the invention said nucleotide spacer sequence is 16 nucleotides in length.

In a preferred embodiment of the invention said nucleotide spacer sequence is 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides in length.

In a preferred embodiment of the invention said nucleotide spacer sequence is at least 40 nucleotides in length.

In a preferred embodiment of the invention said nucleotide spacer sequence is between 40 and 75 nucleotides in length.

In a preferred embodiment of the invention said nucleotide spacer sequence is 40, 45, 50, 55, 60, 65, 70 or 75 nucleotides in length.

In a preferred embodiment of the invention said promoter is a constitutive promoter conferring constitutive expression.

In a preferred embodiment of the invention said promoter is regulatable and includes an inducible or repressible nucleotide element conferring regulatable expression.

In a preferred embodiment of the invention said promoter is a regulatable promoter and includes an inducible nucleotide element conferring regulated expression in response to an inducer.

In an alternative embodiment of the invention said regulatable promoter includes a repressible nucleotide element conferring regulated expression in response to a repressor.

Bacterial expression systems that utilize inducers and repressors of gene expression are well known in the art and include modifications that are well established which enhance induction or repression of gene expression. For example, is laclq carries a mutation in the promoter region of the lacI gene that results in increased transcription and higher levels of Lac repressor within the cells. Moreover, the Ptac, a strong hybrid promoter composed of the −35 region of the trp promoter and the −10 region of the lacUV5 promoter/operator and is strongly inducible.

In a preferred embodiment of the invention the reduction in nucleic acid molecule translation of said oligosaccharyltransferase and/or said carrier polypeptide and/or biosynthetic locus is reduced by at least 10% when compared to a control nucleic acid molecule that encodes said oligosaccharyltransferase and/or said carrier polypeptide and/or biosynthetic locus but does not comprise said spacer nucleotide sequence.

In a preferred embodiment of the invention the reduction in nucleic acid translation is 15%, 20%, 25%, 30%, 35%, 40%, 45%, 50%, 55%, 60%, 65%, 70%, 75%, 80%, 85% or 90% when compared to a control nucleic acid that encodes said recombinant polypeptide but does not comprise said spacer nucleotide sequence.

In a preferred embodiment of the invention said biosynthetic locus is the PgI locus.

Preferably said PgI locus comprises genes encoding said one or more polypeptides selected from the group consisting of: PgIG, PgIF, PgIE, Cj1122c, PgID, PgIC, PgIA, PgIJ, PgII, PgIH, PgIK.

In a further preferred embodiment said nucleic acid molecule encoding one or more polypeptides required for the synthesis of a heterogeneous glycan antigen comprises a sequence as set forth in SEQ ID NO 12, wherein said SEQ ID NO:12 does not include a functional version of PgIB, for example SEQ ID NO 4 or polymorphic sequence variant thereof.

In an alternative embodiment of the invention said attenuated pathogenic bacterial cell is inactivated.

According to a further aspect of the invention there is provided a vaccine or immunogenic composition comprising an attenuated or inactivated pathogenic bacterial cell according to the invention.

In a further preferred embodiment of the invention said vaccine or immunogenic composition includes an adjuvant and/or carrier.

Adjuvants (immune potentiators or immunomodulators) have been used for decades to improve the immune response to vaccine antigens. The incorporation of adjuvants into vaccine formulations is aimed at enhancing, accelerating and prolonging the specific immune response to vaccine antigens. Advantages of adjuvants include the enhancement of the immunogenicity of weaker antigens, the reduction of the antigen amount needed for a successful immunisation, the reduction of the frequency of booster immunisations. Selectively, adjuvants can also be employed to optimise a desired immune response, e.g. with respect to immunoglobulin classes and induction of cytotoxic or helper T lymphocyte responses. In addition, certain adjuvants can be used to promote antibody responses at mucosal surfaces.

Adjuvants can be classified according to their source, mechanism of action and physical or chemical properties. The most commonly described adjuvant classes are gel-type, microbial, oil-emulsion and emulsifier-based, particulate, synthetic and cytokines. More than one adjuvant may be present in the final vaccine product according to the invention. The origin and nature of the adjuvants currently being used or developed is highly diverse. For example, MDP is derived from bacterial cell walls; saponins are of plant origin, squalene is derived from shark liver and recombinant endogenous immunomodulators are derived from recombinant bacterial, yeast or mammalian cells.

There are several adjuvants licensed for veterinary vaccines, such as mineral oil emulsions that are too reactive for human use. Similarly, complete Freund's adjuvant is one of the most powerful adjuvants known.

The vaccine compositions of the invention can be administered by any conventional route, including injection. The administration may be, for example, intravenous, intraperitoneal, intramuscular, intracavity, subcutaneous, or intradermally. The vaccine compositions of the invention are administered in effective amounts. An "effective amount" is that amount of a vaccine composition that alone or together with further doses, produces the desired response. In the case of treating a bacterial disease the desired response is providing protection when challenged by an infective agent.

According to an aspect of the invention there is provided a vaccine composition according to the invention for use in the prevention or treatment of a bacterial infection in a non-human animal subject.

In a preferred embodiment of the invention said vaccine composition prevents or treats two different bacterial infections in said non-human animal subject.

In a further preferred embodiment of the invention said vaccine composition prevents or treats three different bacterial infections in said non-human animal subject.

In a further preferred embodiment said bacterial infections are caused by bacterial species selected from the group consisting of: *Actinobacillus pleuropneumoniae, Escherichia coli, Clostridium perfringens, Campylobacter jejuni, Campylobacter coli, Haemophilus parasuis, Streptococcus suis, Streptococcus uberis, Salmonella typhimurium, Salmonella enterica, Staphylococcus aureus, Mycobacterium bovis, Francisella tularensis, Shigella flexneri, Yersinia enterocolitica, Bordetella bronhiseptica, Brucella abortus, Listeria monocytogenes, Erysipelotrix rhusiopatie* and *Leptospira interrogans*.

In a preferred embodiment of the invention said bacterial infection is the result of a streptococcal infection.

In a preferred embodiment of the invention said bacterial infection is caused by *Escherichia coli, Staphylococcus aureus* and *Streptococcus uberis* and said bacterial infection is mastitis.

In an alternative embodiment of the invention said bacterial infection is caused by *Actinobacillus pleuropneumoniae, Haemophilus parasuis* and *Streptococcus suis* and said bacterial infection is a respiratory infection.

In a further embodiment of the invention said bacterial infection is caused by *Escherichia coli, Campylobacter jejuni* or *Campylobacter coli* and *Clostridium perfringens*.

In a preferred embodiment of the invention said bacterial infection is caused by *Mycoplasma hyopneumoniae*.

In a further preferred embodiment said non-human animal is a livestock animal for example, cattle, sheep, goat, pig, horse, deer, boar, and poultry, for example chicken, fish, for example salmon.

In a further preferred embodiment said animal is a companion animal for example, cat, dog, parrot, rabbit, hamster and guinea pig.

According to a further aspect of the invention there is provided an immunogenic composition for use in the induction of an immune response in a non-human animal species.

In a preferred embodiment of the invention said immune response is the induction of a humoral response, in particular the induction of an opsonic antibody response.

In an alternative embodiment of the invention said immune response is a cell mediated immune response.

According to an aspect of the invention there is provided a cell culture comprising an attenuated pathogenic bacterial cell according to the invention.

According to a further aspect of the invention there is provided a method for the manufacture of an attenuated pathogenic bacterial cell according to the invention comprising the steps:
 i) providing a bacterial cell culture according to the invention;
 ii) providing cell culture conditions; and
 iii) culturing and optionally isolating the attenuated pathogenic bacterial cells from the cell culture.

According to a further aspect of the invention there is provided a cell culture vessel comprising a bacterial cell culture according to the invention.

In a preferred embodiment of the invention said cell culture vessel is a fermentor.

Bacterial cultures used in the process according to the invention are grown or cultured in the manner with which the skilled worker is familiar, depending on the host organism. As a rule, bacteria are grown in a liquid medium comprising a carbon source, usually in the form of sugars, a nitrogen source, usually in the form of organic nitrogen sources such as yeast extract or salts such as ammonium sulfate, trace elements such as salts of iron, manganese and magnesium and, if appropriate, vitamins, at temperatures of between 0° C. and 100° C., preferably between 10° C. and 60° C., while gassing in oxygen.

The pH of the liquid medium can either be kept constant, that is to say regulated during the culturing period, or not. The cultures can be grown batchwise, semi-batchwise or continuously. Nutrients can be provided at the beginning of the fermentation or fed in semi-continuously or continuously. The products produced can be isolated from the bacteria as described above by processes known to the skilled worker, for example by extraction, distillation, crystallization, if appropriate precipitation with salt, and/or chromatography. In this process, the pH value is advantageously kept between pH 4 and 12, preferably between pH 6 and 9, especially preferably between pH 7 and 8.

An overview of known cultivation methods can be found in the textbook Bioprocess technology 1. Introduction to Bioprocess technology (Gustav Fischer Verlag, Stuttgart, 1991) or in the textbook by Storhas (Bioreaktoren and periphere Einrichtungen [Bioreactors and peripheral equipment] (Vieweg Verlag, Brunswick/Wiesbaden, 1994)).

The culture medium to be used must suitably meet the requirements of the bacterial strains in question. Descriptions of culture media for various bacteria can be found in the textbook "Manual of Methods for General Bacteriology" of the American Society for Bacteriology (Washington D.C., USA, 1981).

As described above, these media which can be employed in accordance with the invention usually comprise one or more carbon sources, nitrogen sources, inorganic salts, vitamins and/or trace elements.

Preferred carbon sources are sugars, such as mono-, di- or polysaccharides. Examples of carbon sources are glucose, fructose, mannose, galactose, ribose, sorbose, ribulose, lactose, maltose, sucrose, raffinose, starch or cellulose. Sugars can also be added to the media via complex compounds such as molasses or other by-products from sugar refining. The addition of mixtures of a variety of carbon sources may also be advantageous. Other possible carbon sources are oils and fats such as, for example, soya oil, sunflower oil, peanut oil and/or coconut fat, fatty acids such as, for example, palmitic acid, stearic acid and/or linoleic acid, alcohols and/or polyalcohols such as, for example, glycerol, methanol and/or ethanol, and/or organic acids such as, for example, acetic acid and/or lactic acid.

Nitrogen sources are usually organic or inorganic nitrogen compounds or materials comprising these compounds. Examples of nitrogen sources comprise ammonia in liquid or gaseous form or ammonium salts such as ammonium sulfate, ammonium chloride, ammonium phosphate, ammonium carbonate or ammonium nitrate, nitrates, urea, amino acids or complex nitrogen sources such as cornsteep liquor, soya meal, soya protein, yeast extract, meat extract and others. The nitrogen sources can be used individually or as a mixture.

Inorganic salt compounds which may be present in the media comprise the chloride, phosphorus and sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents comprise dihydroxyphenols such as catechol or protocatechuate and organic acids such as citric acid.

The fermentation media used according to the invention for culturing bacteria usually also comprise other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media compounds heavily depends on the particular experiment and is decided upon individually for each specific case.

Information on the optimization of media can be found in the textbook "Applied Microbiol. Physiology, A Practical Approach" (Editors P. M. Rhodes, P. F. Stanbury, IRL Press (1997) pp. 53-73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by filter sterilization. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, ambient air into the culture. The temperature of the culture is normally 20° C. to 45° C. and preferably 25° C. to 40° C. The culture is continued until formation of the desired product is at a maximum. This aim is normally achieved within 10 to 160 hours.

The fermentation broth can then be processed further. The biomass may, according to requirement, be removed completely or partially from the fermentation broth by separation methods such as, for example, centrifugation, filtration, decanting or a combination of these methods or be left completely in said broth. It is advantageous to process the biomass after its separation.

However, the fermentation broth can also be thickened or concentrated without separating the cells, using known methods such as, for example, with the aid of a rotary evaporator, thin-film evaporator, falling-film evaporator, by reverse osmosis or by nanofiltration. Finally, this concentrated fermentation broth can be processed to obtain the fatty acids present therein.

According to an aspect of the invention there is provided a live pathogenic bacterial cell comprising at least one inactive or mutated gene encoding a membrane polypeptide or membrane associated polypeptide wherein the live pathogenic bacterial cell is attenuated and the attenuation is the result of said gene inactivation or mutation.

In a preferred embodiment of the invention said attenuated bacterial cell is a Gram-positive bacterial cell.

In an alternative preferred embodiment of the invention said attenuated bacterial cell is a Gram-negative bacterial cell.

In a preferred embodiment of the invention said attenuated bacterial pathogenic Gram negative cell is selected from the group: *Escherichia* spp, for example *E. coli*, *E. coli* serogroup 078, *Salmonella* spp, for example *S. typhimurium*, *S. entrica*, *Leptospira* spp, *Francisella* spp, for example *F. tularensis*, *Shigella* spp, for example *S. flexneri*, *Yersinia* spp, for example *Y. enterolitica*, *Bordetella* spp, for example *B. bronchiseptica* and *Brucella* spp, for example *B. abortus*, *Brachyspira* spp. for example *Brachyspira pinosicoli*, *Haemophilus* spp. for example *Haemophilus parasuis*.

In an alternative preferred embodiment of the invention said bacterial pathogenic Gram positive cell is selected from the group: *Listeria* spp, for example *L. monocytogenes*, *Erysipelotrix* spp, for example *E. rhusiopathiae* and *Mycobacterium* spp, for example *M. bovis*.

In an alternative preferred embodiment of the invention said bacterial cell is of the genus *Streptococcus*.

In a preferred embodiment of the invention said bacterial pathogen is selected from the group consisting of: *Streptococcus suis*, *Streptococcus pyogenes*, *Streptococcus equisimilis*, *Streptococcus bovis*, *Streptococcus anginosus*, *Streptococcus sanguinis*, *Streptococcus mitis*, *Streptococcus innuae*, *Streptococcus equi*, *Streptococcus uberus* and *Streptococcus pneumoniae*.

In a preferred embodiment of the invention said bacterial cell is *Streptococcus suis*.

In a preferred embodiment of the invention said bacterial cell is *Mycoplasma hyopneumoniae*.

In a preferred embodiment of the invention said gene is selected from the group consisting of: a gene encoding a sortase and/or a gene encoding a polysaccharide modification enzyme wherein said modification is associated with the inactivation or inhibition of expression of said sortase or polysaccharide modification gene.

In a preferred embodiment of the invention the gene encoding said sortase is encoded by a nucleotide sequence selected from the group consisting of:
   i) a nucleic acid molecule comprising a nucleotide sequence as set forth in SEQ ID NO:1;
   ii) a nucleic acid molecule comprising a nucleotide sequence wherein said sequence is degenerate as a result of the genetic code to the nucleotide sequence defined in (i); and
   iii) a nucleic acid molecule the complementary strand of which hybridizes under stringent hybridization conditions to the nucleotide sequence in i) and ii) above wherein said nucleic acid molecule encodes a sortase.

In a preferred embodiment of the invention the gene encoding said sortase is encoded by a nucleotide sequence selected from the group consisting of:
   i) a nucleic acid molecule comprising a nucleotide sequence as set forth in SEQ ID NO:2;
   ii) a nucleic acid molecule comprising a nucleotide sequence wherein said sequence is degenerate as a result of the genetic code to the nucleotide sequence defined in (i); and
   iii) a nucleic acid molecule the complementary strand of which hybridizes under stringent hybridization conditions to the nucleotide sequence in i) and ii) above wherein said nucleic acid molecule encodes a sortase.

In a preferred embodiment of the invention the gene encoding said polysaccharide modification enzyme is encoded by a nucleotide sequence selected from the group consisting of:
   i) a nucleic acid molecule comprising a nucleotide sequence as set forth in SEQ ID NO:3;
   ii) a nucleic acid molecule comprising a nucleotide sequence wherein said sequence is degenerate as a result of the genetic code to the nucleotide sequence defined in (i); and
   iii) a nucleic acid molecule the complementary strand of which hybridizes under stringent hybridization conditions to the nucleotide sequence in i) and ii) above wherein said nucleic acid molecule encodes a polysaccharide modification enzyme.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF SUMMARY OF THE DRAWINGS

An embodiment of the invention will now be described by example only and with reference to the following figures.

Figure 1A:
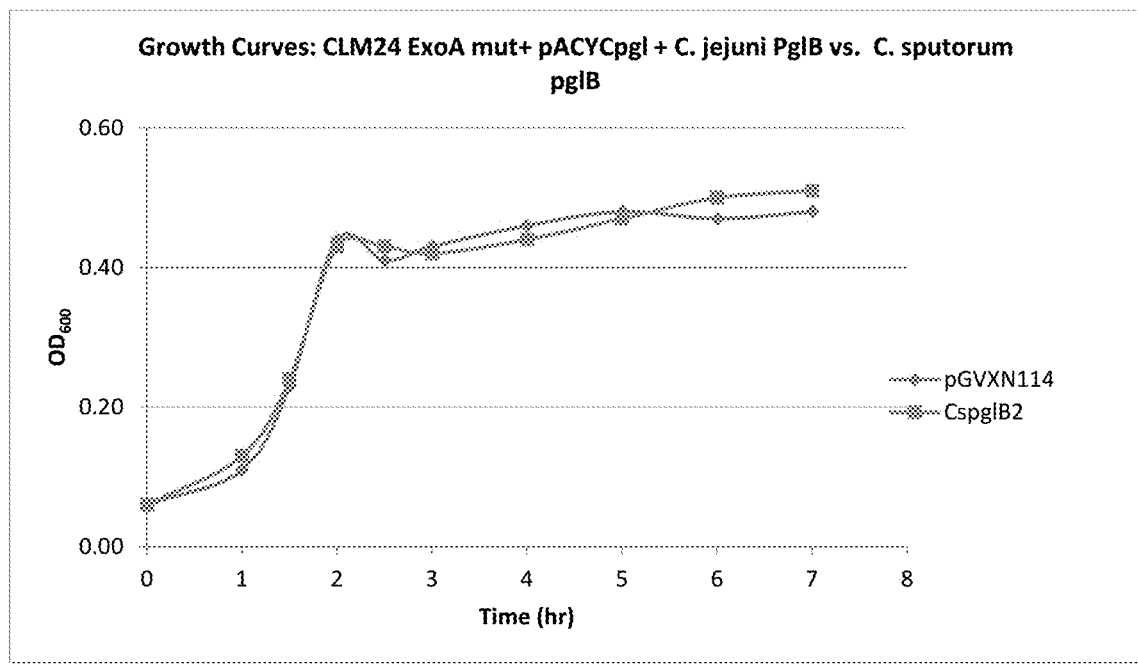
FIGS. 1A and 1B illustrate a growth comparison in *E. coli* CLM24 following induction of expression of *C. jejuni* pgIB and CspgIB2. Growth curves were set up to monitor the optical density of the *E. coli* cells following induction of CspgIB1 or CspgIB2 (FIGS. 1A and B): We found that CspgIB2 and *C. jejuni* pgIB appeared to have very similar toxicity levels.

A codon optimised version of *C. sputorum* pgIB2 was generated by DNA synthesis in the cloning vector pUC57 km and designed to have EcoRI (GAATTC) restriction enzyme sites at the 5' and 3' end of the construct. The plasmid pEXT21 was grown in *E. coli* DH5α cells and purified by plasmid extraction (QIAGEN Ltd UK). 1 µg of pUC57 Km containing CsPgIB2 and 1 µg of pEXT21 were digested with EcoRIHF (New England Biolabs U.K.) cloned into the EcoRI site of the IPTG inducible expression vector pEXT21 to generate the vector pELLA1.

Construction of pELLA2

The gene coding for *C. sputorum* PgIB2 was amplified by PCR with the pTac promoter and LacI repressor from plasmid pEXT21 as a template using accuprime Taq hifi with (SEQ ID NO: 13, 5'-TTTTGCGGCCGCTTC-TACGTGTTCCGCTTCC-3') as forward primer and (SEQ ID NO:14, 5'-TTTTGCGGCCGCATTGCGTTGCGCT-CACTGC-3') reverse primer using the following cycling conditions, 94° C./2 minutes followed by 35 cycles of 94° C. for 30 seconds, 56° C. for 30 seconds and 68° C. for 4 minutes. and ligated into the unique NotI site in pJCUSA1 a Zeocin® resistant transposon where the antibiotic marker is flanked by loxP sites allowing for downstream removal of antibiotic marker from the final target strain via the introduction of the CRE enzyme. It has a pMB1 origin of replication and thus can be maintained in any *E. coli* strain prior to being cut out and transferred along with the Zeocin® resistance cassette using SfiI restriction enzyme digestion and transfer into the pUT delivery vector thus generating a functional transposon. The sequence of the transposon is shown below (SEQ ID NO: 15):

```
5'GGCCGCCTAGGCCGCGGCCGCCTACTTCGTATAGCATACATTATACGA

AGTTATGTCTGACGCTCAGTGGAACGACGCGTAACTCACGTTAAGGGATT

TTGGTCATGATCAGCACGTTGACAATTAATCATCGGCATAGTATATCGGC

ATAGTATAATACGACAAGGTGAGGAACTAAAACATGGCCAAGTTGACCAG

TGCCGTTCCGGTGCTCACCGCGCGCGACGTCGCCGGAGCGGTCGAGTTCT

GGACCGACCGGCTCGGGTTCTCCCGGGACTTCGTGGAGGACGACTTCGCC

GGTGTGGTCCGGGACGACGTGACCCTGTTCATCAGCGCGGTCCAGGACCA

GGTGGTGCCGGACAACACCCTGGCCTGGGTGTGGGTGCGCGGCCTGGACG

AGCTGTACGCCGAGTGGTCGGAGGTCGTGTCCACGAACTTCCGGGACGCC

TCCGGGCCGGCCATGACCGAGATCGGCGAGCAGCCGTGGGGCGGGAGTT

CGCCCTGCGCGACCCGGCCGGCAACTGCGTGCACTTCGTGGCCGAGGAGC

AGGACTGAATAACTTCGTATAGCATACATTATACGAAGTTATGGCCGCCT

AGGCC-3'.
```

The insertion of CspgIB2 into this transposon and transfer into the pUT delivery vector resulted in plasmid pELLA2 and maintained in Transformax *E. coli* strain EC100D pir+ (Cambio U.K.).

Bacterial Conjugation

To enable transfer of the CspgIB2 transposon cargo into the chromosome of a recipient *E. coli* strain or any other bacterium the plasmids pELLA2 was transferred into *E. coli* MFD a diaminopimelic acid (DAP) auxotroph. Growth medium was supplemented with Zeocin® 100 µg/ml and ampicillin 100 µg/ml. Both donor and recipient bacteria were growth until late exponential phase. Bacterial cells were pelleted by centrifugation, washed 3 times with PBS and mixed together in a ratio of 1:3 recipient to donor and spotted on a dry LB agar plate with no antibiotics for 4-8 hrs. The cells were scraped and suspended in PBS and dilutions plated on LB agar with appropriate selection antibiotics to select for transconjugants. Individual colonies were picked up and screened for loss of the pUT backbone and for the presence of the transposon.

Generation of Unmarked pgIB Insertion

The transposon carrying CspgIB2 and loxP recombination sites around a Zeocin® resistance cassette was introduced into PoulVAc *E. coli*. Following selection for Zeocin® resistant colonies, the antibiotic selection marker was removed by introduction via electroporation, the temperature sensitive vector pCRE5 (Reference: Appl Environ Microbiol. 2008 February; 74(4): 1064-1075. Genetic Tools for Select-Agent-Compliant Manipulation of *Burkholderia pseudomallei*. Kyoung-Hee Choi, Takehiko Mima, Yveth Casart, Drew Rholl, Ayush Kumar, Ifor R. Beacham and Herbert P. Schweizer).

PoulVAc *E. coli* was cultured at 28° C. in the presence of kanamycin 50 µg/ml, rhamnose was added to induce expression at 0.2% final concentration and the organism subcultured several times to select for colonies that had lost resistance to Zeocin® but maintained resistance to kanmaycin indicating that the bleomycin resistance gene had been flipped out of the chromosome.

This *E. coli* mutant was then sub-cultured at 42° C. to cure out the pCRE5 plasmid. Screening for colonies that had once again become sensitive to kanamycin confirmed loss of pCRE5 and completed generation of an unmarked inducible copy of pgIB on the chromosome of *E. coli*.

Construction of pELLA3

The pgIB gene from *C. sputorum* was amplified using the primers CsPgIB1fwd: TTTT GAATTCGATTATCGC-CATGGCGTCAAATTTTAATTTCGCTAAA (SEQ ID NO 16) and the reverse primer CsPgIB1 rev: TTTT GAATTC TTATTTTTTGAGTTTATAAATTTTAGTTGAT (SEQ ID NO 17) using Accuprime Taq Hifi and the following cycling conditions 94° C./30 s, followed by 24 cycles of the following conditions 94° C./30 s, 53° C./30 s, 68° C./2 min. The PCR product was cut with the restriction enzyme EcoRI HF for 16 hr at 37° C. The plasmid pEXT21 was also cut with the restriction enzyme EcoRI HF for 16 hr at 37° C. Both plasmid and PCR product were purified with a PCR purification kit (QIAGEN UK) and the plasmid pEXT21 was dephosphorylated by treating with Antarctic phosphatase (NEB UK Ltd) at 37° C. for 1 hr. The enzyme was heat inactivated by heating at 80° C. for 2 min before the plasmid and the insert were ligated together using T4 DNA ligase (Promega UK) and the reaction was incubated overnight at 4° C. The ligation reaction was transformed into *E. coli* Dh10β cells (NEB UK Ltd) and recovered on LB Spectinomycin plates (80 µg/ml). Constructs were then sequenced to confirm that the cloned *C. sputorum* PgIB had not gained any mutations during the cloning process. This new construct was named pELLA3.

In another version of this glycoengineering tool a mariner Himar1 element was modified to carry a unique NotI site between the IR1 and IR2 ends of the transposon. This NotI site was used to enable the integration of the hyaluronan synthase gene and UDP-Glc dehydrogenase encoding genes from *Streptococcus pneumoniae* serotype 3 under control of the erm cassette contained within the Himar1 transposon. The vector used to make the Himar1 based insertions was a derivative of vector pCAM45 (May et al. FEMS Microbiology Letters 2004) with the modification that the R6k origin of replication was removed. This new transposon carrying vector was named pELLA4.

Carrier Polypeptide

Figure 12:
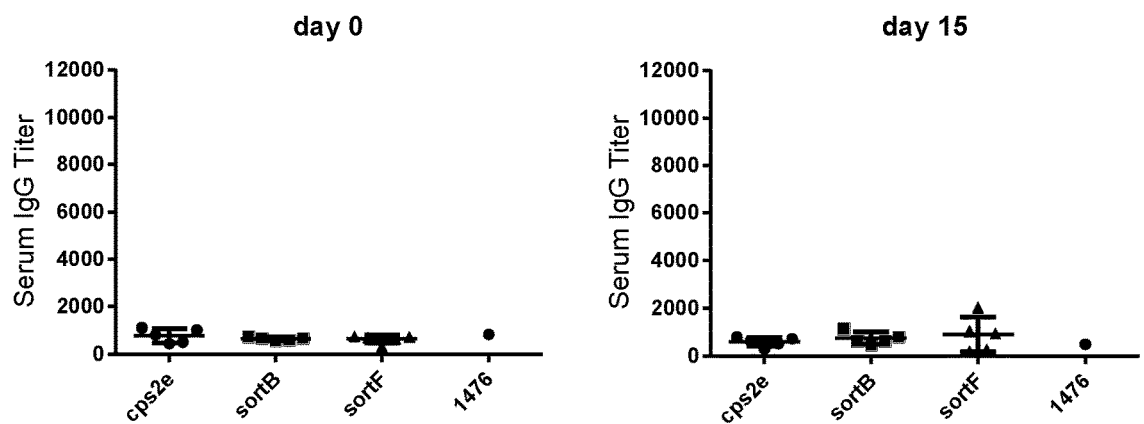

Attenuated bacterial strains are transformed with the plasmid pGVXN150:GT-ExoA encoding a modified carrier polypeptide [GT-ExoA]. The GT-ExoA construct was engineered to express a modified version of *P. aeruginosa* Exotoxin A in the vector pGH and closed into a vector derived from pEC415 using the restriction enzymes NheI and EcoRI (NEB). The synthesized protein contains two internal modifications that allow glycosylation of the protein by PgI, as well as containing four N-glycosylation sequons at the N terminal and an additional 4 at the C terminals glycotags. In addition, a hexa-histidine tag was added to the C-terminus of the protein to facilitate putification and and an *E. coli* DsbA signal peptide was added to the N-terminal sequences enabling Sec-dependent secretion to the periplasm. pGVXN150: GT-ExoA is ampicillin resistant and L-(+)-Arabinose inducible. The construct sequence was then confirmed using Sanger sequences with the primers GTExoA NF (SEQ ID NO 18; GCGCTGGCTGGTTTAGTTT), GTExoA NR (SEQ ID NO 19; CGCATTCGTTCCAGAGGT), GTExoA CF (SEQ ID NO 20; GACAAGGAACAGGCGATCAG) and GTExoA CR (SEQ ID NO 21; TGGTGATGATGGTGATGGTC).

Reducing the Toxicity of PglB

Protein glycan coupling technology requires the use of *Campylobacter jejuni* PglB. This enzyme has 13 transmembrane domain and is toxic when overexpressed in *E. coli*. The pglB gene was originally amplified by PCR with oligonucleotides PglBEcoRI (EcoRI in bold) using the primers (SEQ ID NO 22: AAGAATTCATGTTGAAAAAAGAGTATTTAAAAAACCC) and PglBNcoI-HA (SEQ ID NO 23: AACCATGGTTAAGCGTAATCTGGAACATCGTATGGGTAAATTTTAAGTTTAAAAACCTTAGC), using Pfu polymerase with pACYC(pgl) as template. Oligonucleotide PglBNcoI-HA encodes an HA-tag to follow PglB expression by Western blot. The PCR product was digested with EcoRI and NcoI and cloned in the same sites of vector pMLBAD. The plasmid obtained was named pMAF10. Arabinose-dependent expression of PglB was confirmed by Western blot (Feldman et al. 2005). This construct has been subcloned into the EcoRI site of the vector pEXT21 allowing for IPTG dependant inducible expression of CjpglB. This plasmid and ORF combination has been used for several years in order to produce several glycoconjugate vaccines. In a recent modification using PglB from *Campylobacter sputorum* we have carried out tests and found that the ribosome binding site is encoded within the pEXT21 vector itself. This means that translational efficiency is partly controlled by the distance between the RBS and the ATG start codon of pglB. We noticed that inserting the PglB coding gene into the vector pEXT21 with an extended 10 base pairs of DNA sequence resulted in reduced toxicity of the enzyme and subsequently increased growth in the carrier *E. coli* strain as measured by optical density. Therefore it may be possible to reduce the toxicity of *C. jejuni* PglB by the simple modification of insertion of additional nucleotides before the ATG start codon or alternatively clone the gene further away from the RBS carried within the expression plasmid.

In Vitro Mutagenesis of the *C. jejuni* 81116 pgl Locus Cloned in pACYC184

Mutagenesis of 11 genes in the *C. jejuni* 81116 glycosylation locus cloned in pACYC184 (pACYCpgl) was performed in vitro using a customised EZ::TNtransposon system (Epicentre, Madison, Wis., USA). Briefly, a kanamycin resistance cassette (Trieu-Cuot et al., 1985) lacking a transcriptional terminator and therefore unable to exert downstream polar effects was amplified by PCR and cloned into the multiple cloning site of the vector pMOD™<MCS> (Epicentre). This construct was linearized by ScaI digestion and the kanamycin resistance cassette along with flanking mosaic ends was amplified by PCR using primers FP-1 and RP-1 (Epicentre). The PCR product was combined with plasmid pACYCpgl (Wacker et al., 2002) in an in vitro transposition reaction performed according to manufacturer's instructions (Epicentre). The resultant pool of mutated pACYCpgl plasmids was electroporated into *E. coli* XL1-Blue MRF' (Stratagene) and putative mutants were screened by PCR to identify the location and orientation of the kanamycin cassette. We only used those mutants having the kanamycin resistance cassette inserted with the same transcriptional orientation as the genes of the glycosylation locus, which were also confirmed by sequence analysis.

Pathogenesis of *Streptococcus suis* Mutants and Wild Type P1/7 Strain in Pigs

TABLE 1

Experimental Groups

| GROUP | CHALLENGE | NO | PIG# | 4E RM |
|---|---|---|---|---|
| Group 1 | Δ cps2E | 5 | 1-5 | 7 |
| Group 2 | Δ srtB | 5 | 6-10 | 9 |
| Group 3 | Δ srtF | 5 | 11-15 | 11 |
| Group 4 | Δ 1476 | 5 | 16-20 | 13 |
| Group 5 | WT SS P1/7 (shared w/ SRD121) | 8 | 990-997 | 8-14 (2 pigs/room) |

Nasal swaps and blood samples were taken from the pigs prior to intranasal challenge with *Streptococcus suis* mutant and wild type strains (day 0). The pigs were challenged with 2 ml (1 ml per nostril) of approx. $10^9$ CFU/ml in PBS of *S. suis* mutant and wild type strains (Table 3).

TABLE 3

Titers of inocula:

| | | |
|---|---|---|
| Δ cps2E | (−5) tntc (−6) 250, 176 (−7) 15, 9 | $2.13 \times 10^9$ CFU/ml |
| Δ srtB | (−5) tntc (−6) 122, 102 (−7) 16, 15 | $1.12 \times 10^9$ CFU/ml |
| Δ srtF | (−5) tntc (−6) 146, 170 (−7) 16, 18 | $1.58 \times 10^9$ CFU/ml |
| Δ 1476 | (−5) tntc (−6) 190, 189 (−7) 23, 20 | $1.90 \times 10^9$ CFU/ml |
| P1/7 | (−5) tntc (−6) 63, 66 (−7) 6, 4 | $6.45 \times 10^8$ CFU/ml |

On day 2, 5 and 7 either nasal or nasal and tonsil swabs were taken and immediately plated for bacterial count.

Pigs were observed for clinical signs of severe disease, including lameness, lethargy, neurological symptoms. Samples at necropsy such as SST for blood, nasal swab, tonsil swab, swab of serosa (pericardium, thoracic cavity, abdominal cavity), joint tap or swab (affected joint or hock), CSF tap. Lung lavage was taken and either immediately cultured or frozen, gross lesions were recorded. Samples were collected in 2 ml PBS except lung lavage where 50 ml of PBS were instilled into the lung and collected with a pipette. 100 ul of the samples were plated on TSA blood agar plates.

If presentation was severe enough (dyspneic, paddling and/or does not rise upon human entry into the pen), the pig was euthanized. Otherwise if no clinical signs show pigs were euthanize pigs at day 15 after infection. Serum antibody titre was measured after 15 days of exposure in pigs (FIG. 12).

EXAMPLE 1

The construct pELLA1 was transformed into E. coli CLM24 cells alongside a pEC415 vector coding for Pseudomonas aeruginosa exotoxin A with a single internal glycosylation site and the plasmid pACYCpgIB::km coding for the entire C. jejuni heptasaccharide with a disruption in the pgIB gene by insertion of a miniTn5km2 element. As a comparison the exotoxin A and C. jejuni heptasaccharide coding constructs were transformed into an E. coli CLM24 cell carrying pEXT21pgIB from C. jejuni. 500 ml LB containing 30 μg/ml$^{-1}$ cm, 100 μg/ml$^{-1}$ amp, 80 μg/ml$^{-1}$ spectinomycin were inoculated with 10 ml of an O/N culture of either CLM24 construct combination and incubated with shaking at 37° C. Optical density 600 nm reading were taken at hourly intervals and protein expression induced at an $OD_{600}$ nm of 0.4 by the addition of IPTG 1 mM and L-arabinose 0.2% final concentration. 5 hr post initial induction, 0.2% L-arabinose was added and $OD_{600}$ nm continued to be measured (FIG. 1A).

Figure 1B:
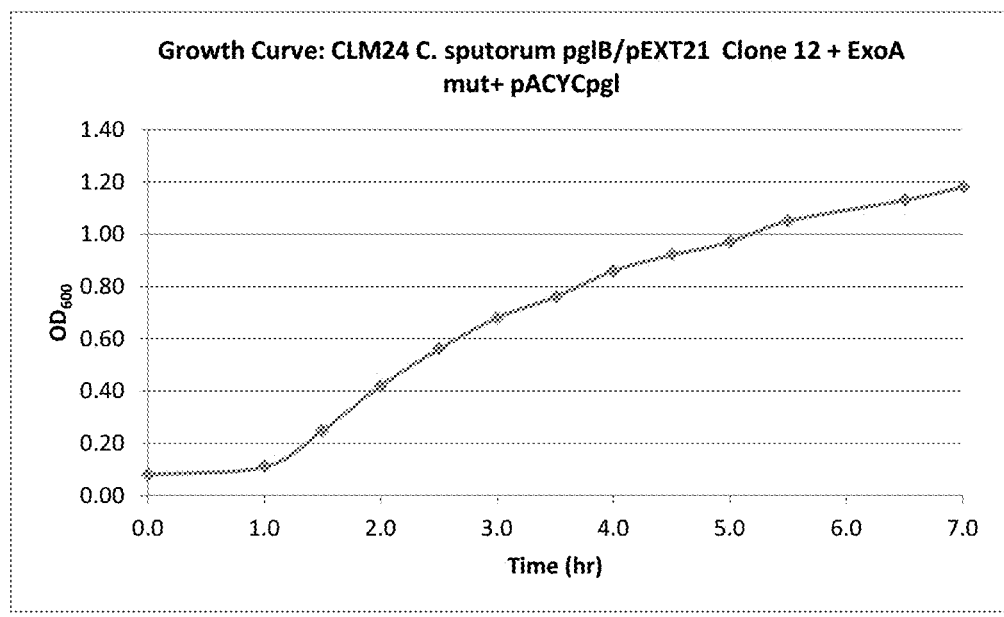

The growth of E. coli CLM24 cells without any induction of protein expression was also measured. This was carried out in the same way as described above for the E. coli CLM24 cells carrying pELLA1 except that no IPTG or L-arabinose was added (FIG. 1B).

EXAMPLE 2

Figure 2:
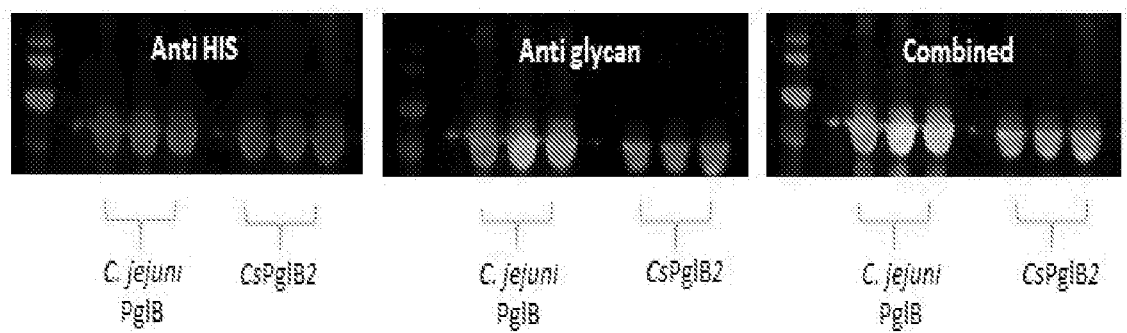
FIG. 2 illustrates glycosylation efficiency test in *E. coli* CLM24 glycosylating exotoxin A carrying a single glycosylation site.

E. coli CLM24 cultures carrying plasmids coding for singly glycosylatable exotoxinA, C. sputorum PgIB2 or C. jejuni PgIB were used to inoculate 500 ml of LB broth. Protein expression was induced as described in example 1 with the modification that the cultures were incubated for a further 16 hr after the second 0.2% L-arabinose addition. At this point cells were pelleted by centrifugation at 4000×g for 30 min and lysed using a high pressure cell homogeniser (Stansted Fluid power) HIS tagged exotoxinA was purified from CLM24 cells using NiNTA binding. Protein was separated on a 12% Bis-tris gel (Invitrogen) before transferring onto a nitrocellulose membrane. This was probed with primary rabbit hr6 anti-campy glycan antibody and mouse anti-HIS. Goat anti-rabbit and anti-mouse infrared dye labelled secondary antibodies were used to enable visualisation of glycoprotein using an Odyssey LI-COR scanner (LI-COR Biosciences UK Ltd) (FIG. 2).

Figure 3:
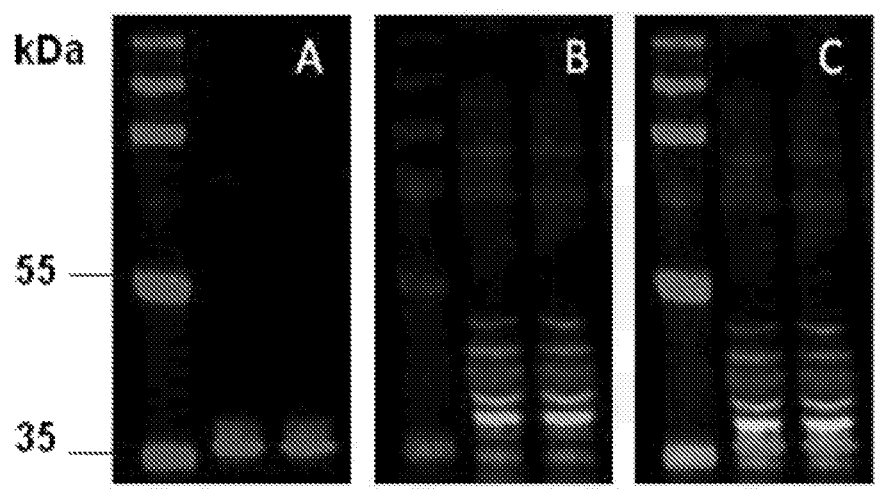
FIG. 3 illustrates *C. jejuni* heptasaccharide glycosylation of CjaA from two independent clones of PoulvaC *E. coli* [bands B and C]. A) Anti-cMyc tag channel only; B) Anti *C. jejuni* heptasaccharide only; C) overlaid cMyc and *C. jejuni* heptasaccharide combined signals.
Figure 4:
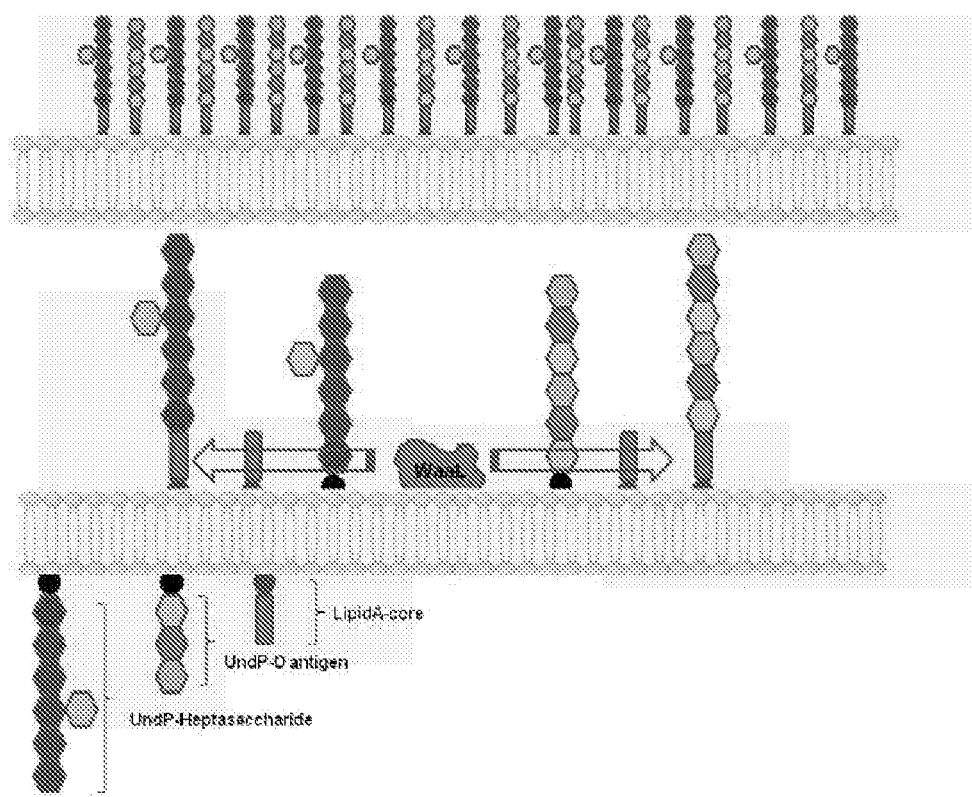
FIG. 4 illustrates formation of a hybrid polysaccharide on the surface of PoulVac *E. coli* and *Salmonella*; and *Streptococcus equi* with the alteration that surface presentation would be via attachment to a phosphatidylglycerol membrane anchor instead of UndPP.

EXAMPLE 3 pACYCpgI was introduced into PouIVAC E. coli by electroporation alongside the plasmid pUA31 coding for a c-Myc tagged tetraglycosylatable L-arabinose inducible CjaA. After 2 inductions with 0.2% L-arabinose and a total of 24 hr incubation at 37° C. with shaking. 1 ml of culture was obtained and centrifuged at 10,000×g for 10 min. The supernatant was discarded and the pellet resuspended in 100 μl of 2×SDS PAGE loading dye. This was boiled for 10 min before 20 μl was loaded into a 12% Bis-Tris gel and transferring onto a nitrocellulose membrane. Samples were probed with mouse anti c-Myc antibody and rabbit hr6 antibody. Goat anti-rabbit and anti-mouse infrared dye labelled secondary antibodies were used to enable visualisation of glycoprotein using an Odyssey LI-COR scanner (LI-COR Biosciences UK Ltd) (FIG. 3).

EXAMPLE 4

Figures 5, 6:
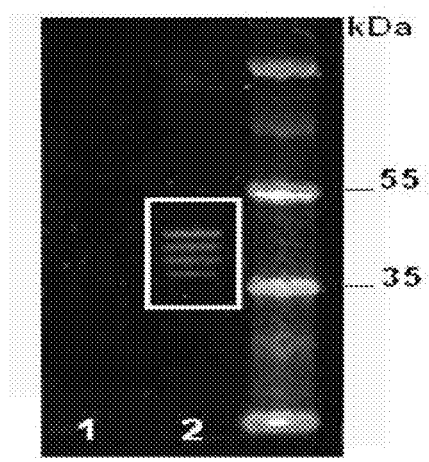
FIG. 5 illustrates a prototype dual poultry glycoconjugate vaccine.
FIG. 6 DNA sequence corresponding to constructs assembled. Green, pEXT21 sequence; purple, EcoRI restriction site; Yellow, 10 nucleotide insertion; red Construction of *C. sputorum* pgIB2 Expression Plasmid pELLA1
Figure 7A:
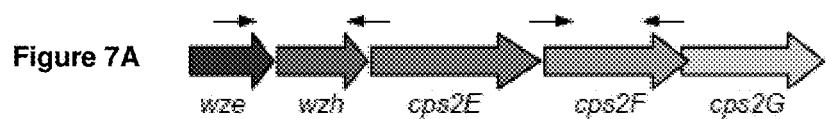
Figure 7B:
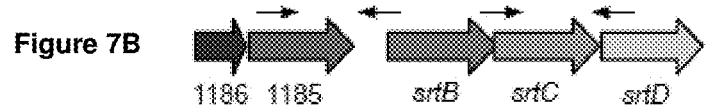
Figure 7C:
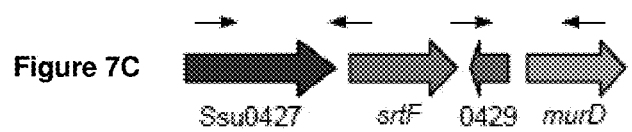
Figure 11:
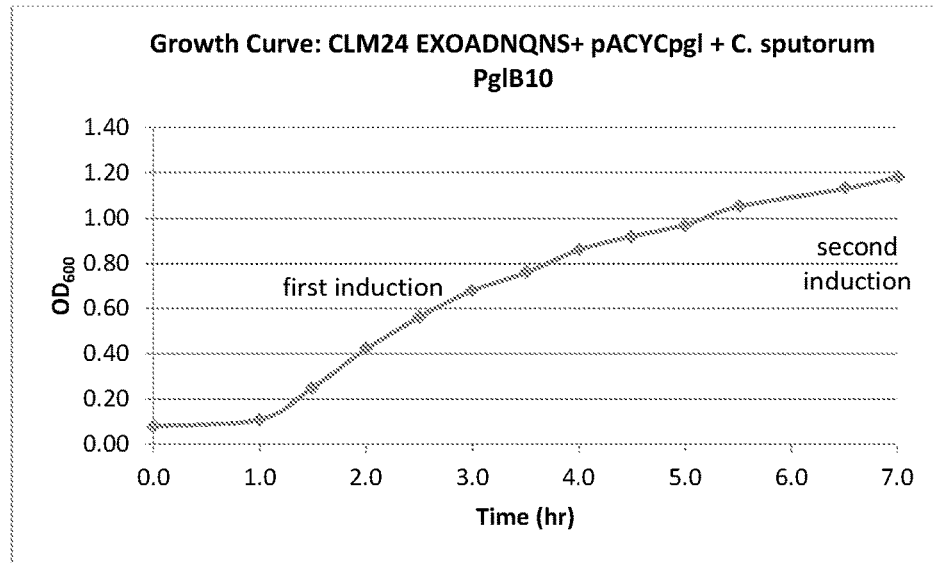

Salmonella Typhimurium strain SL3749 was transformed with pUA31 (coding for the acceptor protein CjaA), pACYCpgI(pgIB::km) (coding for C. jejuni heptasaccharide coding locus but with pgIB knocked out) and pMAF10 (coding for arabinose inducible C. jejuni PgIB). A 10 ml O/N 37° C. shaking culture was prepared and used to inoculate 200 ml of LB broth. This continue to be shaken 37° C. until an OD600 nm of 0.4 was reached. At this point 0.2% L-arabinose was added to induce CjaA and PgIB expression. After 4 hr of incubation L-arabinose was added again to 0.2% final concentration and culture incubated for a further 16 hr at 37° C. with shaking. Bacterial cultures were pelleted by centrifugation at 6000×g for 30 min and resuspended in 30 ml 25 mM Tris, 0.15 M NaCl pH 7.5 (TBS). Cells were lysed using a high pressure cell homogeniser. 2% SDS and 1% Triton X-100 were added and the lysed material incubated for 3 hr at 4° C. with mixing. The material was then centrifuged at 4000×g for 20 min. Pellet was discarded before 300 μl of c-Myc sepharose (Thermo Scientific USA) was added. This was allowed to incubate O/N at 4° C. with mixing. The material was then centrifuged at 4000×g for 10 min and the supernatant removed. 1 ml TBS was added with 0.05% Tween. This was washed 5 times by pulsing at 10,000×g. Protein elution was achieved by the addition of 300 μl 2XSDS loading buffer containing 3 μl DTT and boiled for 10 minutes. Western blot was carried out as described in example 3 (FIG. 5).

EXAMPLE 5

We have used the transposon pELLA2 carrying an IPTG inducible copy of CspgIB to integrate this gene into the chromosomes of glycoengineering E. coli strains W3110, CLM24, CLM37, SΘ874, SCM7, SCM6, SCM3 as well as PouIVAc E. coli and S. typhimurium.

EXAMPLE 6

The E. coli strain CLM24 carrying a plasmid coding for the Campylobacter jejuni heptasaccharide pACYCpgI (without a knock out in pgIB) and an acceptor protein as well as the construct pELLA1 were grown in 50 ml of LB broth containing Cm 30 μg/ml, Sp 80 μg/ml, Amp 100 μg/ml with shaking at 37° C. Optical density readings were taken at $600_{nm}$ at hourly intervals. The growth was compared to that observed when pEXT21 carried C. jejuni pgIB. At an optical density of $OD600_{nm}$ of 0.4 IPTG was added at a final concentration of 1 mM and L-arabinose was added at 0.2% final concentration. Results are shown in FIG. 8 and are the average (mean) of three biological replicates.

EXAMPLE 7

The E. coli strain CLM24 carrying a plasmid coding for the Campylobacter jejuni heptasaccharide pACYCpgI (without a knock out in pgIB) and an acceptor protein as well as the construct pELLA3 were grown in 50 ml of LB broth containing Cm 30 μg/ml, Sp 80 μg/ml, Amp 100 μg/ml with shaking at 37° C. Optical density readings were taken at $600_{nm}$ at hourly intervals. The growth was compared to that observed when pEXT21 carried C. jejuni pgIB. At an optical density of $OD600_{nm}$ of 0.4 IPTG was added at a final concentration of 1 mM and L-arabinose was added at 0.2% final concentration. Results are shown in FIG. 9 and are the average (mean) of three biological replicates.

EXAMPLE 8

Mutagenesis of the Swine and Human Pathogen *Streptococcus suis* Serotype 2 (ss2) in the Absence of a Counter-Selection Marker

*S. suis* serotype 2, is a major pathogen of swine that has recently been reported to have crossed the species barrier, causing infections in humans. The presence of the polysaccharide capsule is considered the major virulence determinant and the gene cps2E is thought to be essential for capsule formation. Other genes of interest to us were the *S. suis* sortases of which there are 6 putative sortases, SrtA-F.

First we identified a plasmid pMTL82151 which is non-replicative in *S. suis* and therefore suitable as a suicide plasmid in this organism. *S. suis* P1/7 competent cells transformed with pMTL82151 could not form colonies on selective plates, while cells transformed with the replicative plasmid pSET1 formed colonies as expected. Allele exchange cassettes for the deletion of the genes csp2E, srtB and srtF were then constructed, with approximately 1.2 kbp regions of homology (with the exception of srtF homology region 2 which contained a 700 bp region of homology to avoid cloning any whole genes which appeared to be toxic to *E. coli*). *S. suis* was transformed with the allele exchange plasmids and chloramphenicol (Cm) resistant single-crossover clones obtained. Single-crossover integrants were passaged without selection and each day colonies were patch plated to determine whether double recombination had occurred. This frequency was high enough that mutants could be easily isolated by the fifth and sixth passage without selection. Cm-sensitive clones were screened by PCR to determine whether they contained mutant or alleles revertant to wild type, mutants of cps2E, srtB and srtFwere isolated and confirmed by Sanger sequencing.

TABLE 2

| Primer name | Sequence (5'-3') | Function (restriction site) |
|---|---|---|
| cps2E R1 | TTACTTACTTCCCTCTCTCAAT ATTTCAATATTCATAGCTCCT (SEQ ID NO 24) | Amplify P1/7 cps2E HA1 |
| cps2E F2 | AGGAGCTATGAATATTGAAATA TTGAGAGAGGGAAGTAAGTAA (SEQ ID NO 25) | Amplify P1/7 cps2E HA2 |
| cps2E F1 | TATATT<u>GAATTC</u>AATTACAAAG ATTACAGGTTTG (SEQ ID NO 26) | Amplify P1/7 cps2E HA1 -1200 bp (EcoRI) |
| cps2E R2 | AGTTCA<u>GGATCC</u>TCCTTTAAAC AACTTCTCATAC (SEQ ID NO 27) | Amplify P1/7 cps2E HA1 +1200 bp (BamHI) |
| cps2E screen F | CTGCGGCTAGTCTCGCTATT (SEQ ID NO 28) | PCR screen P1/7 Δcps2E |
| cps2E screen R | CATGCGCTTCAAATTCATTC (SEQ ID NO 28) | PCR screen P1/7 Δcps2E |
| srtB F1 | AGTTCA<u>CATATG</u>CGGGTGGTA TCGGTACACTT (SEQ ID NO 30) | Amplify P1/7 srtB HA1 Forward |
| srtB R1 | CCTTTTTGTTAATAAGAAAATC AGTTTCTGTATCATAATCCGAA CTTC (SEQ ID NO 31) | Amplify P1/7 srtB HA1 Reverse |
| srtB F2 | GAAGTTCGGATTATGATACAGA AACTGATTTTCTTATTAACAAAA AGG (SEQ ID NO 32) | Amplify P1/7 srtB HA2 Forward |
| srtB R2 | TTCGTAT<u>GGATCC</u>AACTACGGT GACCGGCAAT (SEQ ID NO 33) | Amplify P1/7 srtB HA1 Reverse |
| srtB screen F | GAGAATTGAAGGAAGTGATA (SEQ ID NO 34) | PCR screen P1/7 ΔsrtB |
| srtB screen R | ATATAAGGAGTACAGGTTAG (SEQ ID NO 35) | PCR screen P1/7 ΔsrtB |
| srtF F1 | AGTTCA<u>GCTAGC</u>GGGCAAAGA ATTTCGGTACA (SEQ ID NO 36) | Amplify P1/7 srtF HA1 Forward |
| srtF R1 | CTTTCTGAGGTTCCATGGTAAG GAGCCATTTGATCATGAAAT (SEQ ID NO 37) | Amplify P1/7 srtF HA1 Reverse |
| srtF F2 | ATTTCATGATCAAATGGCTCCT TACCATGGAACCTCAGAAAG (SEQ ID NO 38) | Amplify P1/7 srtF HA2 Forward |

TABLE 2-continued

| Primer name | Sequence (5'-3') | Function (restriction site) |
|---|---|---|
| srtF R2 | TTCGTATGGATCCGTAGTCCAA ATGAGCTACTTAC (SEQ ID NO 39) | Amplify P1/7 srtF HA1 Reverse |
| srtF screen F | GACAAGCCAACTGAAACAAC (SEQ ID NO 40) | PCR screen P1/7 ΔsrtF |
| srtF screen R | AGATTCCCCTGATTTAGCTA (SEQ ID NO 41) | PCR screen P1/7 ΔsrtF |
| M13F | ACTGGCCGTCGTTTTACA (SEQ ID NO 42) | PCR screen |
| M13R | CAGGAAACAGCTATGACC (SEQ ID NO 43) | PCR screen |

HA = homology arm; bp = base pairs; F = Forward; R = Reverse. Underlined sequences correspond to recognition sequences for restriction endonuclease

EXAMPLE 9

The pigs were challenged with the wild type strain of *S. suis* (P1/7), the cps2E mutant which was used as a non-disease-causing control, the srtB and srtF mutants and a mutation in ssu1476 which is a putative sorted protein. Challenge was intranasal, the natural route of infection in pigs.

Onset of clinical signs/necropsy in groups 4-5 was between 3-8 days, whereas groups 1-3 showed no clinical symptoms 15 days after challenge.

REFERENCES

Development of an in vivo Himar1 transposon mutagenesis system for use in *Streptococcus equi* subsp. equi. May J P, Walker C A, Maskell D J, Slater J D. FEMS Microbiol Lett. 2004 September 15; 238(2):401-9.

Mutagenesis of *Streptococcus equi* and *Streptococcus suis* by transposon Tn917. Slater J D, Allen A G, May J P, Bolitho S, Lindsay H, Maskell D J. Vet Microbiol. 2003 May 29; 93(3):197-206.

Genetic analysis of the capsular biosynthetic locus from all 90 pneumococcal serotypes. Bentley S D[1], Aanensen D

TABLE 4

Results - Strep culture at necropsy

| Pig | Onset of clinical signs/necropsy day | Nasal wash | Tonsil swab | BALF | Serosal swab | Joint fluid | CSF | Serum |
|---|---|---|---|---|---|---|---|---|
| 1 | NCS/15 | ? | ? | — | — | — | — | — |
| 2 | NCS/15 | ? | ? | — | — | — | — | — |
| 3 | NCS/15 | ? | ? | — | — | — | — | — |
| 4 | NCS/15 | ? | ? | — | — | — | — | — |
| 5 | NCS/15 | ? | ? | — | — | — | — | — |
| 6 | NCS/15 | ? | ? | — | — | — | — | — |
| 7 | NCS/15 | ? | ? | — | — | — | — | — |
| 8 | NCS/15 | ? | ? | — | — | — | — | — |
| 9 | NCS/15 | ? | ? | — | — | — | — | — |
| 10 | NCS/15 | ? | ? | — | — | — | — | — |
| 11 | NCS/15 | ? | ? | — | — | — | — | — |
| 12 | NCS/15 | ? | ? | — | — | — | — | — |
| 13 | NCS/15 | ? | ? | — | — | — | — | — |
| 14 | NCS/15 | ? | ? | — | — | — | — | — |
| 15 | NCS/15 | ? | ? | — | — | — | — | — |
| 16 | 6/6 | + | ? | — | — | 27 | tntc | tntc |
| 17 | NCS/15 | ? | ? | — | — | — | — | — |
| 18 | 3/3 | ? | ? | — | 300 | Tntc | — | 1 |
| 19 | 6/6 | tntc | ? | — | 2 | — | tntc | tntc |
| 20 | 6/6 | 100 | ? | — | — | — | tntc | — |
| 990 | 5/6 | 100 | ? | 1 | tntc | Tntc | tntc | 148 |
| 991 | 4/4 | ? | ? | — | — | Tntc | — | tntc |
| 992 | 8/8 | ? | ? | — | 2 | Tntc | tntc | 17 |
| 993 | 3/3 | ? | ? | — | — | 10 | tntc | 95 |
| 994 | NCS/15 | ? | ? | — | — | — | — | — |
| 995 | 8/8 | ? | ? | — | 10 | Tntc | tntc | tntc |
| 996 | 5/5 | ? | ? | — | — | Tntc | — | 20 |
| 997 | 6/6 | ? | ? | — | — | — | tntc | 72 |

CS = no clinical signs
? = too many contaminating bacteria to see whether or not Strep colonies were present, plan to do PCR.
+ = Strep present but difficult to estimate numbers with other bacteria present.

M, Mavroidi A, Saunders D, Rabbinowitsch E, Collins M, Donohoe K, Harris D, Murphy L, Quail M A, Samuel G, Skovsted I C, Kaltoft M S, Barrell B, Reeves P R, Parkhill J, Spratt B G. PLoS Genet. 2006 March; 2(3):e31.

Gene content and diversity of the loci encoding biosynthesis of capsular polysaccharides of the 15 serovar reference strains of *Haemophilus parasuis*. Howell K J, Weinert L A, Luan S L, Peters S E, Chaudhuri R R, Harris D, Angen O, Aragon V, Parkhill J, Langford P R, Rycroft A N, Wren B W, Tucker A W, Maskell D J; BRaDP1T Consortium. J Bacteriol. 2013 September; 195(18):4264-73. doi: 10.1128/JB.00471-13. Epub 2013 July 19.

Exploitation of bacterial N-linked glycosylation to develop a novel recombinant glycoconjugate vaccine against *Francisella tularensis*. Cuccui J, Thomas R M, Moule M G, D'Elia R V, Laws T R, Mills D C, Williamson D, Atkins T P, Prior J L, Wren B W. Open Biol. 2013 May 22; 3(5):130002

Characterization of the structurally diverse N-linked glycans of *Campylobacter* species. Jervis A J, Butler J A, Lawson A J, Langdon R, Wren B W, Linton D. J Bacteriol. 2012 May; 194(9):2355-62

The invention claimed is:

1. A vaccine or immunogenic composition, comprising:

a live pathogenic *Streptococcus suis* bacterial cell consisting of a genetically inactivated or mutated sortase B gene wherein said sortase B gene prior to its genetic inactivation or mutation is encoded by:

i) a nucleic acid molecule comprising the nucleotide sequence of SEQ ID NO: 1; or ii) a nucleic acid molecule comprising at least 95% sequence identity SEQ ID NO: 1, and encodes a sortase B, and an adjuvant.

2. The vaccine or immunogenic composition of claim 1, wherein said sortase B gene prior to its genetic inactivation or mutation is encoded by a nucleotide molecule comprising at least 96% sequence identity to the nucleotide sequence of SEQ ID NO: 1 and encodes a sortase B.

3. The vaccine or immunogenic composition of claim 1, wherein said sortase B gene prior to its genetic inactivation or mutation is encoded by a nucleotide sequence comprising at least 97% sequence identity to the nucleotide sequence of SEQ ID NO: 1 and encodes a sortase B.

4. The vaccine or immunogenic composition of claim 1, wherein said sortase B gene prior to its genetic inactivation or mutation is encoded by a nucleotide sequence comprising at least 98% sequence identity to the nucleotide sequence of SEQ ID NO: 1 and encodes a sortase B.

5. The vaccine or immunogenic composition of claim 1, wherein said sortase B gene prior to its genetic inactivation or mutation is encoded by a nucleotide sequence comprising at least 99% sequence identity to the nucleotide sequence of SEQ ID NO: 1 and encodes a sortase B.

6. The vaccine or immunogenic composition of according to claim 1, wherein the sortase B gene prior to its genetic inactivation or mutation is encoded by a nucleotide sequence comprising SEQ ID NO: 1.

7. The vaccine or immunogenic composition of claim 1, wherein the sortase B gene prior to its genetic inactivation or mutation is encoded by a nucleotide sequence consisting of SEQ ID NO: 1.

8. The vaccine or immunogenic composition of claim 1, wherein the mutated sortase B gene comprises a deletion of the sortase B gene.

9. A method to prevent a *Streptococcus suis* infection, comprising administering the vaccine or immunogenic composition according to claim 1 to an animal subject, thereby preventing *Streptococcus suis* infection in the animal subject.

10. The method according to claim 9, wherein said animal subject is a pig.

\* \* \* \* \*

UNITED STATES PATENT AND TRADEMARK OFFICE
CERTIFICATE OF CORRECTION

| | |
|---|---|
| PATENT NO. | : 11,179,454 B2 |
| APPLICATION NO. | : 16/493638 |
| DATED | : November 23, 2021 |
| INVENTOR(S) | : Wren et al. |

It is certified that error appears in the above-identified patent and that said Letters Patent is hereby corrected as shown below:

On the Title Page

Item (12) "Cuccui ,et al." should read:
-- Wren et al. --.

Item (72) Inventors should read:
-- Brendan Wren, London (GB)
Alexandra Faulds-Pain, London (GB) --.

Signed and Sealed this
Sixteenth Day of August, 2022

Katherine Kelly Vidal
*Director of the United States Patent and Trademark Office*

SEQUENCE LISTING

<160> NUMBER OF SEQ ID NOS: 65

<210> SEQ ID NO 1
<211> LENGTH: 888
<212> TYPE: DNA
<213> ORGANISM: Streptococcus suis

<400> SEQUENCE: 1
atgatacaga aaaaatcggg aaaaactaca aagaaaaaaa agaaaagtaa tatcccottt 60 tacttggtat ttttgattgg atttgggatt ttactttatc ctcatgtttc taatttttat 120
tatcgatatg agtcggatca gctgactaat tctttcgacc aagaaaagaa gaccttagct 180
tctgaggagg ttaaggaacg aatagatttg gctcaagctt ttaatgagag tttgaacaat 240
gtggtttcgg aggatccgta taccaaatca cgacatgaag ctggacgggt agagtatgca 300
cggatgctgg aattgcatga aaagataggt tatgttgaaa ttccaaaaat tgaggtcaag 360
cttcctgttt atgcaggaac ttctgagacc gttcttcaaa aaggtgtagg gcatttggaa 420
ggaacatcct taccgattgg ggggagcgat acccatactg tcttaacggc tcatacaggt 480
ttacccaaag ctcggttatt cacagactta acgaaggtaa aaatcggtga tactttctac 540
attcacaata tcgtagaaac attagcgtat gaagtagatc aaatagtggt tgctgaacca 600
actcaatttg aggaattgct ggtcaagcct gggcaggact atgcaacctt gctaacctgt 660
acgccttaca tggtgaatac gcaccgttta ttggtacgcg gtcatcgtat tccttatgtt 720
gcagaagagc atcttaaagc gtctgaaaat gcagagaagc gtattcttat tcgttatctt 780
ctttatgcgc tcggaatgtt tgtcggtatt ttactgattt tcttattaac aaaaaggcgg 840
aaaaataaaa agaaagtgac gagtaatgat gaaacgttca caacttag 888

<210> SEQ ID NO 2
<211> LENGTH: 870
<212> TYPE: DNA
<213> ORGANISM: Streptococcus suis

<400> SEQUENCE: 2
atgatcaaat ggctcaaaaa gaaaggtccg tcttttatca tgccattaat ttttatattg 60
gggattggac tattggctta tccatcggtc agtgattact ggaattcctt ccaccaatca 120
gaggccatca tgtcctattc tgacacagta tcagatatga cagctgacca atacaaagaa 180
atcattgata gtgcgcgcca gtataatcaa gaaaaaccct taaactggaa tgtgactgca 240
tccgacattg aagcctacaa tcaggaattg aatttcaata aagatggcat catgggctat 300
attgagattc ctaaaattga tgtcaagtta tctatatttc atgggacaga cgaaacggtt 360
ttagagactt ctattggaca tctagaagga acatcgttgc ctgtaggagg tttgggaact 420
catagtgtac tttcagggca tcgtgggctc ccatctgccc gtctgttttc tgatttagat 480

| aagttgagag aaggcgatat atttaccatt cacgttctca atgaaacact aacttacaaa | 540 |
| gtggaccaga ttcgagtggt tgagccatca gatttatcgg ctcttaccat ggaacctcag | 600 |
| aaagacttat tgactttggt aacctgtaca ccctacggta ttaatacaca taggctatta | 660 |
| gttcgtggct atcgtattga aaatgttaat ggtagtgctt tggttacctc tgatgctatc | 720 |
| caaattaaag caattttttat tgctccattt atcgcaactc caattctatt tgtaatctta | 780 |
| atttatattt ttataacaac tagtaaaaca tttcgttctc ggaataggaa tcaagtgttg | 840 |
| gatgattttt tagttcccaa gaaattttga | 870 |

<210> SEQ ID NO 3
<211> LENGTH: 1380
<212> TYPE: DNA
<213> ORGANISM: Streptococcus suis

<400> SEQUENCE: 3

| atgaatattg aaataggata tcgccaaacg aaattggcat tgtttgatat gatagcagtt | 60 |
| acgatttctg caatcttaac aagtcatata ccaaatgctg atttaaatcg ttctggaatt | 120 |
| tttatcataa tgatggttca ttattttgca ttttttatat ctcgtatgcc ggttgaattt | 180 |
| gagtatagag gtaatctgat agagtttgaa aaaacattta actatagtat aatatttgta | 240 |
| atttttctta tggcagtttc atttatgtta gagaataatt tcgcactttc aagacgtggt | 300 |
| gccgtgtatt tcacattaat aaacttcgtt ttggtatacc tatttaacgt aattattaag | 360 |
| cagtttaagg atagctttct attttcgaca acctatcaaa aaagacgat tctaattaca | 420 |
| acggctgaac tatgggaaaa tatgcaagtt ttatttgaat cagatatact atttcaaaaa | 480 |
| aatcttgttg cattggtaat tttaggtaca gaaatagata aaattaattt accattaccg | 540 |
| ctctattatt ctgttgaaga agctatagag ttttcaacaa gggaagtggt cgactacgtc | 600 |
| tttataaatt taccaagtga atattttgac ttaaagcaat tagtttcaga cttttgagttg | 660 |
| ttaggtattg atgtaggcgt tgatattaat tcattcggtt ttactgtgtt gaagaataaa | 720 |
| aaaatccaaa tgctaggtga ccatagcatc gtcacttttt ccacaaattt ttataagcct | 780 |
| agtcacatct tgatgaaacg actttttagat atacttggag cagtagtcgg gttaattatt | 840 |
| tgtggtatag tttctatttt gttaattcca attattcgta gagatggtgg accagccatt | 900 |
| tttgctcaga aacgagttgg acagaatgga cgcatattta cattctacaa gtttcgttcg | 960 |
| atgtttgttg atgccgaggt acgtaagaaa gaattaatgg ctcaaaacca gatgcaaggt | 1020 |
| gggatgttca aaatgggacaa cgatcctaga attactccaa ttggacactt catacgaaaa | 1080 |
| acaagtttag atgagttacc acaatttat aatgttctaa ttggagatat gagtctagtc | 1140 |
| ggtacccgtc cgcctacagt tgatgaattt gaaaaatata ctcctagtca aaagagaaga | 1200 |
| ttgagtttta aaccagggat tacaggtctt tggcaagtga gcggaagaag tgatatcaca | 1260 |
| gattttaatg aagtcgttag gctggaccta acatacattg ataattggac catctggtca | 1320 |
| gacattaaga ttttattgaa gacagtgaaa gttgtattgt tgagagaggg aagtaagtaa | 1380 |

<210> SEQ ID NO 4
<211> LENGTH: 2142
<212> TYPE: DNA
<213> ORGANISM: Campylobacter jejuni

<400> SEQUENCE: 4

| atgttgaaaa aagagtattt aaaaaacccct tatttagttt tgtttgcgat gattgtatta | 60 |

```
gcttatgttt ttagtgtatt ttgcaggttt tattgggttt ggtgggcaag tgagtttaac      120
gagtattttt tcaataatca attaatgatc atttcaaacg atggctatgc ttttgctgag      180
ggcgcaagag atatgatagc aggttttcat cagcctaatg atttgagtta ttatggatct      240
tctttatcta cgcttactta ttggcttttat aaaatcacac cttttctctt tgaaagtatc      300
attttatata tgagtacttt tttatcttct ttggtggtga ttcctattat tttactagct      360
aatgaataca aacgcccttt aatgggcttt gtagctgctc ttttagcaag tgtagcaaac      420
agttattata atcgcactat gagtgggtat tatgatacgg atatgctggt aattgtttta      480
cctatgttta ttttatttttt tatggtaaga atgattttaa aaaagacttt ttttcattg      540 attgccttgc cattatttat aggaatttat ctttggtggt atccttcaag ttatacttta      600
aatgtagctt taattggact tttttaatt tatacactta ttttttcatag aaaagaaaag      660 atttttttata tagctgtgat tttgtcttct cttactcttt caaatatagc atggttttat      720
caaagtgcca ttatagtaat acttttttgct ttatttgctt tagagcaaaa acgcttaaat      780
tttatgatta taggaatttt aggtagtgca actttgatat ttttgatttt aagtggtggg      840
gttgatccca tactttatca gcttaaattt tatattttta gaagcgatga agtgcgaat      900 ttaacacagg gctttatgta ttttaatgtt aatcaaacca tacaagaagt tgaaaatgta      960
gattttagcg aatttatgcg aagaattagt ggtagtgaaa ttgttttctt gttttctttg      1020
tttggttttg tatggctttt gagaaaacat aaaagtatga ttatgggcttt acctatattg      1080 gtgcttgggt ttttagccct aaaaggagga cttagattta ccatttattc tgtacctgta      1140
atggctttag gatttggttt tttattgagc gagtttaagg ctatattggt taaaaaatat      1200
agccaattaa cttcaaatgt ttgtattgtt tttgcaacta ttttgacttt ggctccagta      1260
tttatccata tttacaacta taaagcgcca acagtttttt ctcaaaatga agcatcatta      1320
ttaaatcaat taaaaatat agccaataga gaagattatg tggtaacttg gtgggattat      1380
ggttatcctg tgcgttatta tagcgatgtg aaaactttag tagatggtgg aaagcattta      1440
ggtaaggata atttttttccc ttctttttct taagtaaag atgaacaagc tgcagctaat      1500
atggcaagac ttagtgtaga atatacagaa aaaagctttt atgctccgca aaatgatatt      1560
ttaaaatcag acatttttaca agccatgatg aaagattata atcaaagcaa tgtggattta      1620
tttctagctt cattatcaaa acctgatttt aaaatcgata caccaaaaac tcgtgatatt      1680
tatctttata tgcccgctag aatgtctttg atttttttcta cggtggctag ttttttcttt      1740
attaatttag atacaggagt tttggataaa ccttttacct ttagcacagc ttatccactt      1800
gatgttaaaa atggagaaat ttatcttagc aacggagtgg ttttaagcga tgattttaga      1860
agttttaaaa taggtgataa tgtggttct gtaaatagta tcgtagagat taattctatt      1920
aaacaaggtg aatacaaat cactccaatc gatgataagg ctcagttttta tattttttat      1980 ttaaaggata gtgctattcc ttacgcacaa tttattttaa tggataaaac catgtttaat      2040
agtgcttatg tgcaaatgtt ttttttggga aattatgata gaatttatt tgacttggtg      2100 attaattcta gagatgctaa agtttttaaa cttaaaattt aa                         2142
```

<210> SEQ ID NO 5
<211> LENGTH: 2133
<212> TYPE: DNA
<213> ORGANISM: Campylobacter sputorum

<400> SEQUENCE: 5

```
atgtcaaatt ttaatttcgc taaatttcta aataaattac ctagactttc taaacatact       60
```

```
atattaatga ttgttttagc tgtttgtttt gggatatttt gcagatttta ctgggtagtt      120
tgggctagtg cttatcccca ttttatatgg aatgatgaac ttatgataag tacaaatgat      180
ggatatgcat ttgctgaggg cacaagagat atgatagctg ttttcatca accaaacgat       240 ctttcttact atggctcatc tctttctaca cttagcatgt ggctatatag cattttgcca      300
ttttcattag aaactatact tttgtatatg agtacatttt tatctccact attagctgtg     360
cctttgatac ttataggtaa agaactaaac gcttcaaaag ctggatttat agctgcactt     420
ctagctgttg ttgcaaatag ttattataat agaacaatga gtggatatta tgatacagat     480
atgctaaata ttactcttcc tatgatggtt ttttggagca taacaagact tgttcaaaga     540
aaagagagag taaatttaat atttattcca gttttatgg cgatatatgg atggtggtat      600
ccatcttctt actcactatt actcgcaatg attgggatgt tgttttata taccattgtt     660 tttgaaagat atgaaaaact aaactatgaa gctatggttt ttatgatttt ggcaatcaca    720
agctttccta tacaaatcaa atttattata gttattattt tgtatgcttt gatctatttt    780
tatcaaagat ttttgataa aaagtaata tttgcattaa ttatagcttc atcaatatgc      840
tttatatggc ttggcggatt aaatcctata cttttaaca ttaaatttta tatatttaga     900
gacattgcag atagtggtga tactgttttt aaattttca atgtaaatca acaataaga       960 gaaagttccg cgatagattt taatacagtt gcaactagga ttagtgggca tttgatagta   1020
tttttggtat ctattgtagg atatatttta tttataaaaa acaataaaat tttactacta   1080
actttaccga ttctatttttt aggtcttatg tcatttaaaa gtggtttaag atttacaata   1140
tactcagttc cagtaatggc ccttggtttt ggttattttg ttatgtattg ttttacaaag   1200
atagatataa aagatcgttt tttaggttat gcatttttat ttgttgtaac atttagtgca   1260
ttatatccat ctttaaaaca tatttatgat tataaggtat ttcctgtttt tacacatagc   1320
gaagttgaaa gtttggatga tttaaaaaat attgcaaaaa gagaagatta tgtgctttct   1380
tggtgggatt atggttatcc aataagatat tattctgatg taaaaactct catagatgga   1440
ggaaaacatc taggaagtga taacttcgca gttagctttg cacttggaag cgatcaaaac   1500
agctctgcaa atatggcaag attagaagtt gagtatacag aaagaaatta tgaggaaaaa   1560
tttggattaa atttaaaaca gattatgaaa gattataatg ctacaaatgt taatgagttt   1620
ttattatcat taaaagatgc aaatttagct ctgccaaagc aaacaagaga tatttattac   1680
tatttaccag atagaatgat atacatatat ccaacagtgc tagctttttc tagacttgat   1740
ttgacaacag ggcaagaatt tgctgagccg ttttttatag ttagtgagag attttcagct   1800
acaaatgata tcaaataat gttaaataat aatgttatat taagtagtga tggcactaaa    1860
ttatcaataa atgaaactc ttatagtgta aatacatatg tagaaacaag ttatgatcaa     1920
aatgaaaaat taaatgtaaa ttattttaac atagatccaa atagcaattt ttatgtgatt   1980
tttatgaaag attatttgag aattttggtt ttagataaaa cttatatga tagtgcgtat   2040 attcaacttt ttgtattaga aaattatgat aaaaatttat ttgaaccagt gatttttaaac   2100 ggatcaacta aaatttataa actcaaaaaa tga                                  2133
```

<210> SEQ ID NO 6  
<211> LENGTH: 2133  
<212> TYPE: DNA  
<213> ORGANISM: Campylobacter Sputorum

<400> SEQUENCE: 6

```
atgagtaatt ttaattttgc caaatttctg aacaagctgc ctagactaag caaacatacc       60
atcctgatga tcgtgctggc ggtgtgcttt ggcatctttt gtcgcttta ttgggttgtg       120
tgggcgagtg cgtatccaca ttttatttgg aatgatgaac tgatgatctc tacaaatgat      180
ggctatgcgt ttgcggaagg tacacgcgat atgattgccg gctttcatca gccgaatgat      240
ctgtcatatt atggtagttc actgtccact ttaagcatgt ggctgtatag catcctgccg      300
ttttcattag aaaccatctt actgtatatg tcaacgtttc tgagtccact gctggcagtt      360
ccgttaatct taatcggtaa agaactgaat gcgtctaaag caggctttat tgcagccctg      420
ctggcagttg tggccaatag ctattataat cgcaccatgt caggctatta tgatacggat      480
atgctgaata tcaccttacc gatgatggtg ttttggagca tcacccgcct ggttcagcgc      540
aaagaacggg ttaatctcat ctttattcca gtgtttatgg ccatctatgg ttggtggtat      600
ccatcttcat attcactgct gctggccatg atcggcatgt tgtgctgta taccatcgtg       660
tttgaacgct atgaaaaact gaattatgaa gcaatggtgt ttatgattct ggcaatcact      720
agctttccga ttcagatcaa gtttatcatc gtgatcattc tgtatgcgtt aatctatttt      780
tatcagcgct ttttcgataa aaaagttatc tttgccttaa tcattgcaag tagcatttgc      840
tttatttggt taggcggctt aaatccaatc ctgtttaata tcaaattta tatctttcgc       900
gacatagcgg attcaggcga tacggtgttt aaattcttca atgtgaatca gaccattcgc      960
gaaagtagcg ccatcgattt taatacagtt gcgacccgca tctcaggtca tctgattgtg     1020
tttctggtga gcatcgtggg ctatatcctg tttatcaaaa acaacaagat tttactgctg     1080
accttaccga tcctgtttct gggtctgatg tcgtttaaaa gcggcctgcg ctttacaatc     1140
tatagcgttc ctgtaatggc gttaggcttt ggctattttg tgatgtattg ctttacgaaa     1200
atcgacatca aagatcgctt tctgggctat gcctttctgt tgtggtgac ctttagtgcc      1260
ctgtatccgt cactgaaaca tatctatgat tacaaggtgt tccagtgtt tacacatagc      1320
gaagtggaaa gcctggatga tctgaaaaat attgccaaac gcgaagatta tgtgctgtct     1380
tggtgggatt atggctatcc gattcgctat tatagcgatg ttaaaacact gatcgatggc     1440
ggtaaacatc taggttcaga taattttgcc gtgagctttg cactgggcag cgatcagaat     1500
agtagtgcaa atatggcccg cttagaagtg gaatatacgg aacgcaatta tgaagaaaaa     1560
tttggtctga atctgaaaca gatcatgaaa gattataatg caaccaatgt gaatgagttt     1620
ctgctgtctc tgaaagatgc caacctggcc ctgcctaaac agacacgcga tatatattat     1680
tatctgccgg atcgcatgat ctatatctat cctacagtgt tagccttag tcgcctggat      1740
ctgacgacgg gccaggaatt tgcagaaccg ttttcatcg tgagcgaacg ctttagtgca     1800
accaatgata tcagatcat gttaaacaac aatgtgattc tttcatcaga tggaacaaaa      1860
ctgtcaatca atggcaatag ctattcagtt aatacttatg tagaaaccag ctacgatcag     1920
aacgaaaaac tgaatgttaa ttattttaat atcgatccga atagcaattt ttatgtgatc     1980
tttatgaaag attatctgcg catccttagtt ctggataaaa ccctgtatga tagcgcgtat    2040
atccagctgt tgtgctgga aaattatgat aaaaatctgt ttgaaccagt catcctgaat     2100
ggtagtacga aaatctataa gctgaaaaaa taa                                 2133
```

<210> SEQ ID NO 7
<211> LENGTH: 713
<212> TYPE: PRT
<213> ORGANISM: Campylobacter jejuni

<400> SEQUENCE: 7

```
Met Leu Lys Lys Glu Tyr Leu Lys Asn Pro Tyr Leu Val Leu Phe Ala
1               5                   10                  15
Met Ile Val Leu Ala Tyr Val Phe Ser Val Phe Cys Arg Phe Tyr Trp
            20                  25                  30
Val Trp Trp Ala Ser Glu Phe Asn Glu Tyr Phe Phe Asn Asn Gln Leu
        35                  40                  45
Met Ile Ile Ser Asn Asp Gly Tyr Ala Phe Ala Glu Gly Ala Arg Asp
    50                  55                  60
Met Ile Ala Gly Phe His Gln Pro Asn Asp Leu Ser Tyr Tyr Gly Ser
65                  70                  75                  80
Ser Leu Ser Thr Leu Thr Tyr Trp Leu Tyr Lys Ile Thr Pro Phe Ser
                85                  90                  95
Phe Glu Ser Ile Ile Leu Tyr Met Ser Thr Phe Leu Ser Ser Leu Val
            100                 105                 110
Val Ile Pro Ile Ile Leu Leu Ala Asn Glu Tyr Lys Arg Pro Leu Met
        115                 120                 125
Gly Phe Val Ala Ala Leu Leu Ala Ser Val Ala Asn Ser Tyr Tyr Asn
    130                 135                 140
Arg Thr Met Ser Gly Tyr Tyr Asp Thr Asp Met Leu Val Ile Val Leu
145                 150                 155                 160
Pro Met Phe Ile Leu Phe Phe Met Val Arg Met Ile Leu Lys Lys Asp
                165                 170                 175
Phe Phe Ser Leu Ile Ala Leu Pro Leu Phe Ile Gly Ile Tyr Leu Trp
            180                 185                 190
Trp Tyr Pro Ser Ser Tyr Thr Leu Asn Val Ala Leu Ile Gly Leu Phe
        195                 200                 205
Leu Ile Tyr Thr Leu Ile Phe His Arg Lys Glu Lys Ile Phe Tyr Ile
    210                 215                 220
Ala Val Ile Leu Ser Ser Leu Thr Leu Ser Asn Ile Ala Trp Phe Tyr
225                 230                 235                 240
Gln Ser Ala Ile Ile Val Ile Leu Phe Ala Leu Phe Ala Leu Glu Gln
                245                 250                 255
Lys Arg Leu Asn Phe Met Ile Ile Gly Ile Leu Gly Ser Ala Thr Leu
            260                 265                 270
Ile Phe Leu Ile Leu Ser Gly Gly Val Asp Pro Ile Leu Tyr Gln Leu
        275                 280                 285
Lys Phe Tyr Ile Phe Arg Ser Asp Glu Ser Ala Asn Leu Thr Gln Gly
    290                 295                 300
Phe Met Tyr Phe Asn Val Asn Gln Thr Ile Gln Glu Val Glu Asn Val
305                 310                 315                 320
Asp Phe Ser Glu Phe Met Arg Arg Ile Ser Gly Ser Glu Ile Val Phe
                325                 330                 335
Leu Phe Ser Leu Phe Gly Phe Val Trp Leu Leu Arg Lys His Lys Ser
            340                 345                 350
Met Ile Met Ala Leu Pro Ile Leu Val Leu Gly Phe Leu Ala Leu Lys
        355                 360                 365
Gly Gly Leu Arg Phe Thr Ile Tyr Ser Val Pro Val Met Ala Leu Gly
    370                 375                 380
Phe Gly Phe Leu Leu Ser Glu Phe Lys Ala Ile Leu Val Lys Lys Tyr
385                 390                 395                 400
Ser Gln Leu Thr Ser Asn Val Cys Ile Val Phe Ala Thr Ile Leu Thr
                405                 410                 415
```

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
            435                 440                 445

Asn Arg Glu Asp Tyr Val Val Thr Trp Trp Asp Tyr Gly Tyr Pro Val
        450                 455                 460

Arg Tyr Tyr Ser Asp Val Lys Thr Leu Val Asp Gly Lys His Leu
465                 470                 475                 480

Gly Lys Asp Asn Phe Phe Pro Ser Phe Ser Leu Ser Lys Asp Glu Gln
                    485                 490                 495

Ala Ala Ala Asn Met Ala Arg Leu Ser Val Glu Tyr Thr Glu Lys Ser
                500                 505                 510

Phe Tyr Ala Pro Gln Asn Asp Ile Leu Lys Ser Asp Ile Leu Gln Ala
            515                 520                 525

Met Met Lys Asp Tyr Asn Gln Ser Asn Val Asp Leu Phe Leu Ala Ser
            530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
                580                 585                 590

Thr Phe Ser Thr Ala Tyr Pro Leu Asp Val Lys Asn Gly Glu Ile Tyr
            595                 600                 605

Leu Ser Asn Gly Val Val Leu Ser Asp Asp Phe Arg Ser Phe Lys Ile
        610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe
            675                 680                 685

Leu Gly Asn Tyr Asp Lys Asn Leu Phe Asp Leu Val Ile Asn Ser Arg
        690                 695                 700

Asp Ala Lys Val Phe Lys Leu Lys Ile
705                 710

<210> SEQ ID NO 8
<211> LENGTH: 710
<212> TYPE: PRT
<213> ORGANISM: Campylobacter sputorum

<400> SEQUENCE: 8

Met Ser Asn Phe Asn Phe Ala Lys Phe Leu Asn Lys Leu Pro Arg Leu
1               5                   10                  15

Ser Lys His Thr Ile Leu Met Ile Val Leu Ala Val Cys Phe Gly Ile
            20                  25                  30

Phe Cys Arg Phe Tyr Trp Val Val Trp Ala Ser Ala Tyr Pro His Phe
        35                  40                  45

Ile Trp Asn Asp Glu Leu Met Ile Ser Thr Asn Asp Gly Tyr Ala Phe
50 55 60

Ala Glu Gly Thr Arg Asp Met Ile Ala Gly Phe His Gln Pro Asn Asp
65 70 75 80

```
Leu Ser Tyr Tyr Gly Ser Ser Leu Ser Thr Leu Ser Met Trp Leu Tyr
            85                  90                  95

Ser Ile Leu Pro Phe Ser Leu Glu Thr Ile Leu Leu Tyr Met Ser Thr
            100                 105                 110

Phe Leu Ser Pro Leu Leu Ala Val Pro Leu Ile Leu Ile Gly Lys Glu
            115                 120                 125

Leu Asn Ala Ser Lys Ala Gly Phe Ile Ala Ala Leu Leu Ala Val Val
        130                 135                 140

Ala Asn Ser Tyr Tyr Asn Arg Thr Met Ser Gly Tyr Tyr Asp Thr Asp
145                 150                 155                 160

Met Leu Asn Ile Thr Leu Pro Met Met Val Phe Trp Ser Ile Thr Arg
                165                 170                 175

Leu Val Gln Arg Lys Glu Arg Val Asn Leu Ile Phe Ile Pro Val Phe
            180                 185                 190

Met Ala Ile Tyr Gly Trp Trp Tyr Pro Ser Ser Tyr Ser Leu Leu Leu
        195                 200                 205

Ala Met Ile Gly Met Phe Val Leu Tyr Thr Ile Val Phe Glu Arg Tyr
    210                 215                 220

Glu Lys Leu Asn Tyr Glu Ala Met Val Phe Met Ile Leu Ala Ile Thr
225                 230                 235                 240

Ser Phe Pro Ile Gln Ile Lys Phe Ile Ile Val Ile Ile Leu Tyr Ala
                245                 250                 255

Leu Ile Tyr Phe Tyr Gln Arg Phe Phe Asp Lys Lys Val Ile Phe Ala
            260                 265                 270

Leu Ile Ile Ala Ser Ser Ile Cys Phe Ile Trp Leu Gly Gly Leu Asn
        275                 280                 285

Pro Ile Leu Phe Asn Ile Lys Phe Tyr Ile Phe Arg Asp Ile Ala Asp
    290                 295                 300

Ser Gly Asp Thr Val Phe Lys Phe Phe Asn Val Asn Gln Thr Ile Arg
305                 310                 315                 320

Glu Ser Ser Ala Ile Asp Phe Asn Thr Val Ala Thr Arg Ile Ser Gly
                325                 330                 335

His Leu Ile Val Phe Leu Val Ser Ile Val Gly Tyr Ile Leu Phe Ile
            340                 345                 350

Lys Asn Asn Lys Ile Leu Leu Leu Thr Leu Pro Ile Leu Phe Leu Gly
        355                 360                 365

Leu Met Ser Phe Lys Ser Gly Leu Arg Phe Thr Ile Tyr Ser Val Pro
    370                 375                 380

Val Met Ala Leu Gly Phe Gly Tyr Phe Val Met Tyr Cys Phe Thr Lys
385                 390                 395                 400

Ile Asp Ile Lys Asp Arg Phe Leu Gly Tyr Ala Phe Leu Phe Val Val
                405                 410                 415

Thr Phe Ser Ala Leu Tyr Pro Ser Leu Lys His Ile Tyr Asp Tyr Lys
            420                 425                 430

Val Phe Pro Val Phe Thr His Ser Glu Val Glu Ser Leu Asp Asp Leu
        435                 440                 445

Lys Asn Ile Ala Lys Arg Glu Asp Tyr Val Leu Ser Trp Trp Asp Tyr
    450                 455                 460

Gly Tyr Pro Ile Arg Tyr Tyr Ser Asp Val Lys Thr Leu Ile Asp Gly
465                 470                 475                 480

Gly Lys His Leu Gly Ser Asp Asn Phe Ala Val Ser Phe Ala Leu Gly
                485                 490                 495
```

Ser Asp Gln Asn Ser Ser Ala Asn Met Ala Arg Leu Glu Val Tyr
            500                 505                 510

Thr Glu Arg Asn Tyr Glu Glu Lys Phe Gly Leu Asn Leu Lys Gln Ile
        515                 520                 525

Met Lys Asp Tyr Asn Ala Thr Asn Val Asn Glu Phe Leu Leu Ser Leu
    530                 535                 540

Lys Asp Ala Asn Leu Ala Leu Pro Lys Gln Thr Arg Asp Ile Tyr Tyr
545                 550                 555                 560

Tyr Leu Pro Asp Arg Met Ile Tyr Ile Tyr Pro Thr Val Leu Ala Phe
                565                 570                 575

Ser Arg Leu Asp Leu Thr Thr Gly Gln Glu Phe Ala Glu Pro Phe Phe
            580                 585                 590

Ile Val Ser Glu Arg Phe Ser Ala Thr Asn Asp Asn Gln Ile Met Leu
        595                 600                 605

Asn Asn Asn Val Ile Leu Ser Ser Asp Gly Thr Lys Leu Ser Ile Asn
    610                 615                 620

Gly Asn Ser Tyr Ser Val Asn Thr Tyr Val Glu Thr Ser Tyr Asp Gln
625                 630                 635                 640

Asn Glu Lys Leu Asn Val Asn Tyr Phe Asn Ile Asp Pro Asn Ser Asn
                645                 650                 655

Phe Tyr Val Ile Phe Met Lys Asp Tyr Leu Arg Ile Leu Val Leu Asp
            660                 665                 670

Lys Thr Leu Tyr Asp Ser Ala Tyr Ile Gln Leu Phe Val Leu Glu Asn
        675                 680                 685

Tyr Asp Lys Asn Leu Phe Glu Pro Val Ile Leu Asn Gly Ser Thr Lys
    690                 695                 700

Ile Tyr Lys Leu Lys Lys
705                 710

<210> SEQ ID NO 9
<211> LENGTH: 840
<212> TYPE: DNA
<213> ORGANISM: Pseudomonas aeruginosa

<400> SEQUENCE: 9

```
atgaaaaaaa tacttctaag tgttttaacg gcctttgttg cagtagtatt ggctgcttgt      60
ggaggaaatt ctgactctaa aactttaaat tctcttgata agatcaagca aaatggagtt     120
gttaggattg gggtatttgg cgataaacca ccttttggtt atgtggatga aaaaggaaac     180
aatcaaggct atgatatagc tttagctaaa cgcatagcaa agaactttt tggcgatgaa     240 aataaggtgc aatttgttct tgttgaagct gcaaataggg ttgagttttt aaaatcaaat     300
aaagtagata ttattttggc taattttact caaactccgc aaagggcaga gcaggttgat     360
ttttgctcgc cttatatgaa ggtagcttta ggcgtagctg taccaaagga tagtaatata     420
actagcgtag aagatttaaa agataaaacc ttgcttttaa acaaaggcac aacagcagat     480
gcttatttta cgcaaaatta tcctaatatt aaaactttaa aatatgatca aaataccgaa     540
acctttgccg cttttgatgga taaagagagc gatgctttaa gtcatgataa taccttactt     600
tttgctgggg tgaaagatca tcctgatttt aaaatgggta ttaaagagtt aggtaacaaa     660
gatgttatcg caccagcggt taaaaaggc gataaagaac ttaagaatt tatcgataat     720 ttgatcatca aactaggcca agagcagttt tttcacaagg cttatgatga aactttaaaa     780
gctcattttg gagatgatgt taaggccgat gatgtagtga ttgaaggtgg aaaaatttaa     840
```

```
<210> SEQ ID NO 10
<211> LENGTH: 1104
<212> TYPE: DNA
<213> ORGANISM: Campylobacter jejuni

<400> SEQUENCE: 10
atgaaattat tcaaaaaaa tactatttta gctttaggtg ttgtgctttt actcactgct      60
tgcagcaaag aagaagcacc aaaaatacaa atgccgcctc aacctgtaac aaccatgagt     120
gctaaatctg aagatttacc acttagtttt acttaccctg ctaaacttgt cagtgattat     180
gatgtcatta taaagcctca agttagtggc gtaatagaaa ataaactttt taaagctgga     240
gataaagtaa aaaaaggaca acattattt attatagaac aagacaaatt taaagctagt     300
gttgattcgg cttacggaca agctttgatg gctaaggcaa cttcgaaaa tgcaagcaag     360 gattttaatc gttctaaagc tcttttagt aaaagtgcaa tctctcaaaa ggaatacgac     420
tcttctcttg ctacatttaa caattcaaaa gctagtctag caagtgctag agcacagctt     480
gcaaatgcaa gaattgatct agatcatacc gaaataaaag ctccttttga tggtactata     540
ggagatgctt tagttaatat aggagattat gtaagtgctt caacaactga actagttaga     600
gttacaaatt taaatcctat ttcgcagat ttctttattt cagatacaga taaactaaat     660
ttagtccgca atactcaaaa tggaaaatgg gatttagaca gcattcatgc aaatttaaat     720
cttaatggag aaaccgttca aggcaaactt tattttattg attctgttat agatgctaat     780
agtggaacag taaaagccaa agctatattt gacaacaaca actcaacact tttaccaggt     840
gcttttgcaa caattacttc agaaggtttt atacaaaaaa atggctttaa agtgcctcaa     900
atagctgtta acaaaatca aaatgatgtt tatgttcttc ttgttaaaaa tggaaaagta     960
gaaaaatctt ctgtacatat aagctaccaa acaatgaat atgccattat tgacaaagga    1020
ttacaaaatg gcgataaaat catttttagat aactttaaaa aaattcaagt tggtagcgaa    1080
gttaaagaaa ttggagcaca ataa                                           1104

<210> SEQ ID NO 11
<211> LENGTH: 2112
<212> TYPE: DNA
<213> ORGANISM: Pseudomonas aeruginosa

<400> SEQUENCE: 11
atgaaaaaga tttggctggc gctggctggt ttagttttag cgtttagcgc tagcgatcag      60
aacgcgaccg cggtgaccaa aaatgccaca ggtggcgatc aaaacgccac cggcggtgac     120
cagaatgcga cagccgccga ggaagccttc gacctctgga cgaatgcgc caaggcctgc     180 gtgctcgacc tcaaggacgg cgtgcgttcc agccgcatga gcgtcgaccc ggccatcgcc     240
gacaccaacg gccagggcgt gctgcactac tccatggtcc tggagggcgg caacgacgcg     300
ctcaagctgg ccatcgacaa cgccctcagc atcaccagcg acggcctgac catccgcctc     360
gaaggcggcg tcgagccgaa caagccggtg cgctacagct acacgcgcca ggcgcgcggc     420
agttggtcgc tgaactggct ggtaccgatc ggccacgaga agccctcgaa catcaaggtg     480
ttcatccacg aactgaacgc cggtaaccag ctcagccaca tgtcgccgat ctacaccatc     540
gagatgggca cgagttgct ggcgaagctg gcgcgcgatg ccaccttctt cgtcagggcg     600
cacgagagca acgagatgca gccgacgctc gccatcagcc atgccggggt cagcgtggtc     660
atggctcagg cccagccgcg ccgggaaaag cgctggagcg aatggggcag cggcaaggtg     720
ttgtgcctgc tcgacccgct ggacggggtc tacaactacc tcgcccagca gcgctgcaac     780
```

```
ctcgacgata cctgggaagg caagatctac cgggtgctcg ccggcaaccc ggcgaagcat        840
gacctggaca tcaaggataa taataattct actcccacgg tcatcagtca tcgcctgcat        900
ttccccgagg gcggcagcct ggccgcgctg accgcgcacc aggcctgcca cctgccgctg        960
gaggccttca ctcgtcatcg ccagccgcgc ggctgggaac aactggagca gtgcggctat       1020
ccggtgcagc ggctggtcgc cctctacctg gcggcgcgac tgtcgtggaa ccaggtcgac       1080
caggtgatcc gcaacgccct ggccagcccc ggcagcggcg gcgacctggg cgaagcgatc       1140
cgcgagcagc cggagcaggc ccgtctggcc ctgaccctgg ccgccgccga gagcgagcgc       1200
ttcgtccggc agggcaccgg caacgacgag gccggcgcgg ccagcgccga cgtggtgagc       1260
ctgacctgcc ccgtcgccaa agatcaaaat agaactaaag gggaatgcgc gggcccggcg       1320
gacagcggcg acgccctgct ggagcgcaac tatcccactg gcgcggagtt cctcggcgac       1380
ggcggcgacg tcagcttcag cacccgcggc acgcagaact ggacggtgga gcggctgctc       1440
caggcgcacc gccaactgga ggagcgcggc tatgtgttcg tcggctacca cggcaccttc       1500
ctcgaagcgg cgcaaagcat cgtcttcggc ggggtgcgcg cgcgcagcca ggacctcgac       1560
gcgatctggc gcggttttcta tatcgccggc gatccggcgc tggcctacgg ctacgcccag       1620
gaccaggaac ccgacgcgcg cggccggatc cgcaacggtg ccctgctgcg ggtctatgtg       1680
ccgcgctgga gtctgccggg cttctaccgc accggcctga ccctggccgc gccggaggcg       1740
gcgggcgagg tcgaacggct gatcggccat ccgctgccgc tgcgcctgga cgccatcacc       1800
ggccccgagg aggaaggcgg gcgcgtgacc attctcggct ggccgctggc cgagcgcacc       1860
gtggtgattc cctcggcgat ccccaccgac ccgcgcaacg tcgcggcgga cctcgacccg       1920
tccagcatcc ccgacaagga acaggcgatc agcgccctgc cggactacgc cagccagccc       1980
ggcaaaccgc cgcgcgagga cttgaaggat cagaacgcga ccggcggtga ccaaaatgcc       2040
acaggtggcg atcaaaacgc caccggcggt gaccagaatg cgacagtcga ccatcaccat       2100
catcaccatt ga                                                           2112

<210> SEQ ID NO 12
<211> LENGTH: 14645
<212> TYPE: DNA
<213> ORGANISM: Campylobacter jejuni

<400> SEQUENCE: 12
atgaaaattc ttattagcgg tggtgcaggt tatataggtt ctcatacttt aagacaattt         60
ttaaaaacag atcatgaaat ttgtgtttta gataatcttt ctaagggttc taaaatcgca        120
atagaagatt tgcaaaaaac aagagctttt aaattttttcg aacaagattt aagtgatttt        180
caaggcgtaa aagcattgtt tgagagagaa aaatttgacg ctattgtgca ttttgcagca        240
agcattgaag ttttttgaaag tatgcaaaat cctttaaaat attatatgaa caacactgtt        300
aatacgacaa atctcatcga aacttgtttg caaactggag tgaataaatt tatattttct        360
tcaacggcgg ccacttatgg cgaaccacaa actcccgttg tgagcgaaac aagtcccttta       420 gcacctatta atccttatgg gcgtagtaag cttatgagtg aagaagtttt gcgtgatgca        480
agtatggcaa atcctgaatt taagcattgt atttttaagat attttaatgt tgcaggtgct       540
tgtatggatt atactttagg acaacgctat ccaaaagcga ctttgcttat aaaagttgca        600
gctgaatgtg ccgcaggaaa acgtgataaa cttttcatat ttggcgatga ttatgataca        660
aaagatggta cttgcataag agattttatc catgtagata tatttcaag tgcacattta        720 gcggctttgg attatttaaa agagaatgaa agcaatgttt ttaatgtagg ttatggacat        780
```

```
ggttttagcg taaaagaagt gattgaagcg atgaaaaaag ttagcggagt ggattttaaa      840
gtagaacttg ccccacgccg tgcgggtgat cctagtgtat tgattctga tgcaagtaaa       900 atcagaaatc ttacttcttg gcagcctaaa tatgatgatt tagagcttat ttgtaaatct      960
gcttttgatt gggaaaaaca gtgttaaaaa aactttttt tatttaagc aaggaagata       1020 aaaattttt attttcttg cttgttttt cagtatttgt ttcttttata gaaacttttg       1080
cgatttcttt ggtaatgcct tttatcactt tggctagtga tttttcttat tttgatcgta    1140
ataaatattt aatcagccta aaagaatatc ttaatatccc tgttttgaa atcattgttt      1200 attttggagt ggggcttatt gttttttatg tatttagagc tttgttaaat gcgtattatt     1260
ttcatctttt ggcaagattt tctaaaggac gttatcatgc gatcgcttat aaggtttttt    1320 ctaaatttt aaatattaat tatgaaaaat ttactcaaaa aaatcaatct gaaatttaa      1380 agtccattac aggggaagtt tataatctaa gcactatgat ttcatcattt ttactttga     1440 tgagtgaaat ttttgtagtg cttttgcttt atgcttaat gcttttgatt aattataaaa     1500
tcactttatt tttaagtatt tttatggtgt taaatgcttt tattttagtg aaaattttaa    1560
gccctatcat taaaaaagca ggactaagac gcgaagaagc gatgaaaaat ttcttcgaaa    1620
ttttaaatac aaatttaaat aattttaaat ttatcaagct taaaaccaaa gaagatggag   1680
tattaagtct ttttaaagca caaagtgaag cttttttctaa agcaaatatt accaatgaaa   1740
gcgtagctgc ggtgcctaga atttatcttg aaggaatagg cttttgtgtg cttgtttta    1800 tcgtggtatt tttggttttg aaaaatgaaa gtgatatttc aggtatttta tccacgattt    1860 ctattttgt tttagcgctt tatcgcttaa tgccaagcgc aaatcgtatt atcacaagtt    1920
atcatgattt gctttattat cattcttctt tgaatattat ttatcaaaat ttaagacaag   1980
aagaagaaaa tttgggcgag ggaaaattaa gttttaatca agagcttaaa atttgcaatc    2040
ttagctttgg ttatgaggga aaaaaatatt tatttaaaaa tcttaattta aacattaaaa    2100
aaggtgaaaa atcgctttt atagggggaga gtggttgtgg aaaaagtacc ttagtagatc   2160
ttatcatagg acttttaaaa ccaaaagaag ggcaaatttt aattgataag caagaattaa    2220
atgcaagtaa tgcaaaaaat tatcgccaaa aaataggcta tatcccgcaa aatatctatc    2280 ttttaatga tagcatagct aaaaatatca cttttggaga tgcggttgat gaagaaaaac     2340
ttaataaggt tatcaaacaa gcaaatttag agcattttat aaaaaattta cctcaaggag   2400
ttcagacaaa agtaggcgat gggggagta atttaagcgg gggacaaaaa caacgcatag    2460
ctatagcaag ggctttgtat ttagagcctg aaatttagt gcttgatgaa gcaacttctg    2520
cgcttgatac tcaaagtgaa gcaaaaatca tggatgaaat ttataaaatt tctaaagata   2580
aaaccatgat tattatcgca catcgccttt ctacgataac gcaatgtgat aaggtttatc    2640
gtttagaaca cggtaagctt aaagaggaga atgatgaaa ataagcttta ttatcgcaac    2700
tttaaattca ggaggcgctg agcgtgtttt agtaaccta gctaatgcgc tttgcaaaga    2760
gcatgaagta agtattatta aatttcatac aggagaatct ttttataagc ttgaaaatga    2820
agttaaagtt acaagtttag aacaatttag atttgacacg ctttatcata aaatcgcaag    2880
tcgttttaag aaatttttg ccttaagaaa ggctttaaaa gaaagtaagg ctgatgtttt    2940
tatttctttt ttggatacaa ctaatattgc ttgtattcta gctaatatag gacttaaaac    3000
tccactcatc attagcgagc atagtaatga agcgtattta aaacctaaaa cttggcgttt    3060
tttaagaagg gtaagctatc cttttttgtga tgctttaagt gtgcttggaa gcagtgataa   3120
```

-continued

```
ggtgtattat gaaagatttg taaaaagggt taagctttta ttaaaccctt gtcattttag    3180
cgatgaaatt cctttgatt ctagttttga aaaagaaaat ttggttcttt ttatagggcg    3240
tttagatcac aacaaaaacc ctgtaatgtt tttaaaagct atagcacatt tggataaaaa    3300
tttgcaagaa aattataaat ttgttatagc aggagatgga gagttaaggc aagaacttga    3360
atacaaggta aaatctttag gaataaaagt tgattttta ggacgcgttg aaaatgtcaa    3420
ggctctttat gaaaaagcaa aagtgctttg cctttgttct tttgtagagg gtttgccaac    3480
ggttttaatt gaaagtttgt atttgaggt ttgtagaatt tcaagttctt attataatgg    3540
tgctaaggat ttaatcaaag ataatcatga tgggcttttg gtaggttgtg atgatgaaat    3600
agcacttgct aaaaaacttg aacttgtttt aaatgatgaa aattttagaa aagaacttgt    3660
aaataatgcc aaacaaaggt gtaaagactt tgaaatttct aacatcaaag aagaatggct    3720
taagcttata gtcgaggtta aaaatgccta aactttctgt tatagtgcca acttttaatc    3780
gtcaagtttt gttagaaaag gctattaaaa gcatacaaaa tcaagatttt aaagatttag    3840
aaatcattgt aagcgatgat aattctagtg atgatactaa aagtgtggtg caaaatttac    3900
aaaaagatga tgatcgcatt aagtattttt taaatcaaaa ttacaaacaa ggcccaaatg    3960
gcaataaaaa caatggctta gatcaagcaa gtggcgagtt tgtaactttt ttagatgatg    4020
atgatgagct tttatctggg gctttaagta ccttgatgca aaaagcaaat gagggttatg    4080
ctcatgtttt tggaaattgt ttgatagaaa aagaaggaaa tttaagcaag gaatttagcg    4140
gtaagggctt ggaaaagat agtgaaattt ctaaaaaaga ttttttaatg gctaaattta    4200
gcggagagtt ttttctgtt tttaaaaaat ctctacttga aaacaagcgt tttaatgaag    4260
aattttatgg caatgaagcc acgctttggg taaatttata caaggaaaaa agttttata    4320
tccataaggc ttttaggatt tataggattt ttaggcaaga tagcgtgact ttaggggcga    4380
gtaaaaatgc tcataggggtg tatttgggat atttagagct tgctaaaatt ttagaaaatg    4440
aacttagaat gagtaaggat aaagattata aaaaaacttg tgcgagttat tataaaatgg    4500
cagcttatta tgcaaaactt gcaaaaaatt ataaagctct ttataagtgt ttgtttaaaa    4560
gcctgagtat aaaaatcaac gctcctgctt tgatattact cattttaagt ataattccaa    4620
ataatatgat tgaaaaatta tcaaaaattc gggtggcttt atgcaaaaat taggcatttt    4680
tatttattct ttaggaagtg gtggtgctga aagagttgtg gcgactttat tgcctatttt    4740
aagtttgaaa tttgaagtgc atttgatttt aatgaatgat aaaatttctt atgaaattcc    4800
agagtgtcaa attcattttt tagaatgttc aaaacctagt gaaaatccta ttttgaaatt    4860
tttaaaacta cctttttttgg ctttaaaata taaaaaactt tgcagaaatt taggcattga    4920
tacagaattt gttttttaa atcgacctaa ttatatagcc ttaatggcaa gaatgtttgg    4980
aaacaaaact cgccttgtga tcaatgaatg cactacgcca agtgtgatgt atgcgaaaaa    5040
taatttaat tctttggcaa ataaattttt aatttctttg ctttacccaa agctgatttt    5100
aatcttgcct aattctaagg gaaatttaga agatttagtg caaaatttta gtataaatcc    5160
aaaaaaatgt gaaatttat acaatgccat cgatttagaa aatatagagc aaaaagctct    5220
tgaagatgta gctttaaaag ataaatttat tttaagtgta ggcaggcttg ataaaggtaa    5280
aaatcatgct ttattaattc gtgcttatgc aagattgaaa acagatttaa agcttgtgat    5340
ttaggtgaa ggtgtgctta agatgagct tttagctttg attaaagagt taaatttaga    5400
agaaaaggtt ttgcttttag gatttgataa taatccttat aaatacatgg ctaaatgcga    5460
attttttgct tttgcttctg tatttgaagg cttttcaaat gttttaattg aaagcttagc    5520
```

```
ttgttcttgt gcggtggttt gcactgatca taaaagtggc gcaagagagc tttttggcga    5580
tgatgaattt ggacttttag tagaagtaga taatgaaaac tccatgtttc agggtttaaa    5640
gactatgctt gaagacgata aattaagaaa agcgtataaa aataaggcta aaactagggc    5700
taaagctttt gataaagtaa aaattgcacg cgatgctttg aaatatttat taggataaaa    5760
gatgttgaaa aaagagtatt taaaaaaccc ttatttagtt ttgtttgcga tgattatatt    5820
agcttatgtt tttagtgtat tttgcaggtt ttattgggtt tggtgggcaa gtgagtttaa    5880
tgagtatttt ttcaataatc agttaatgat catttcaaat gatggctatg cttttgctga    5940
gggcgcaaga gatatgatag caggttttca tcagcctaat gatttgagtt attatggatc    6000
ttctttatcc gcgcttactt attggcttta taaaatcaca ccttttttctt ttgaaagtat    6060
cattttatat atgagtactt ttttatcttc tttggtggtg attcctacta ttttgctagc    6120
taacgaatac aaacgtcctt aatgggcttt gtagctgct cttttagcaa gtatagcaaa     6180
cagttattat aatcgcacta tgagtgggta ttatgatacg gatatgctgg taattgtttt    6240
gcctatgttt atttattttt ttatggtaag aatgatttta aaaaaagact ttttttcatt    6300
gattgccttg ccgttatttta taggaattta tctttggtgg tatccttcaa gttatacttt    6360
aaatgtagct ttaattggac tttttttaat ttatacactt attttttcata gaaaagaaaa    6420
gattttttat atagctgtga ttttgtcttc tcttactctt tcaaatatag catggtttta    6480
tcaaagtgcc attatagtaa acttttttgc tttattcgcc ttagagcaaa aacgcttaaa    6540
ttttatgatt ataggaattt taggtagtgc aactttgata ttttttgattt taagtggtgg    6600
ggttgatcct atactttatc agcttaaatt ttatatttt agaagtgatg aaagtgcgaa      6660
tttaacgcag ggctttatgt attttaatgt caatcaaacc atacaagaag ttgaaaatgt    6720
agatcttagc gaatttatgc gaagaattag tggtagtgaa attgttttt tgttttcttt      6780
gtttggtttt gtatggcttt tgagaaaaca taaaagtatg attatggctt tacctatatt    6840
ggtgcttggg ttttttagcct taaaaggggg gcttagattt accatttatt ctgtacctgt    6900
aatggcctta ggatttggtt ttttattgag cgagtttaag gctataatgg ttaaaaaata    6960
tagccaatta acttcaaatg tttgtattgt ttttgcaact attttgactt tagctccagt    7020
atttatccat atttcaaact ataaagcgcc aacagttttt tctcaaaatg aagcatcatt    7080
attaaatcaa ttaaaaaata tagccaatag agaagattat gtggtaactt ggtgggatta    7140
tggttatcct gtgcgttatt atagcgatgt gaaaacttta gtagatggtg gaaagcattt    7200
aggtaaggat aattttttcc cttctttttgc tttaagcaaa gatgaacaag ctgcagctaa    7260
tatggcaaga cttagtgtag aatatacaga aaaagctttt atgctccgc aaaatgatat     7320
tttaaaaaca gacattttgc aagccatgat gaaagattat aatcaaagca atgtggattt    7380
gtttctagct tcattatcaa aacctgattt taaaatcgat acgccaaaaa ctcgtgatat    7440
ttatctttat atgcccgcta gaatgtcttt gattttttct acggtggcta gttttttcttt    7500
tattaattta gatacaggag ttttggataa accttttacc tttagcacag cttatccact    7560
tgatgttaaa aatggagaaa tttatcttag caacggagtg gttttaagcg atgattttag    7620
aagttttaaa ataggtgata atgtggtttc tgtaaatagt atcgtagaga ttaattctat    7680
taaacaaggt gaatacaaaa tcactccaat tgatgataag gctcagtttt atattttta    7740
tttaaaggat agtgctattc cttacgcaca atttattta atggataaaa ccatgtttaa     7800
tagtgcttat gtgcaaatgt ttttttttagg aaattatgat aagaatttat ttgacttggt    7860
```

```
gattaattct agagatgcta aggttttaa  acttaaaatt taagggttga aaatgagaat    7920 aggatttta  tcacatgcag gagcaagtat ttatcatttt agaatgccta ttataaaagc    7980 attaaagat  agaaaagatg aagttttgt  tatagtgccg caagatgaat acacgcaaaa    8040
acttagagat cttggtttaa aagtaattgt ttatgagttt tcaagagcta gtttaaatcc    8100
ttttgtagtt ttaaagaatt ttttatct  tgctaaggtt ttaaaaatt  taaatcttga    8160 tcttattcaa agtgcggcac acaaaagcaa tacctttgga attttagcgg caaaatgggc    8220
aaaaattcct tatcgttttg ctttggtaga aggcttggga tctttttata tagatcaagg    8280
ttttaaggca aatttagtac gttttgttat taataatctt tataaattaa gttttaaatt    8340
tgcacaccaa tttattttg  tcaatgaaag taatgccgag tttatgcgga atttaggact    8400
taaggaaaat aaaatttgtg tgataaaatc cgtagggatc aatttaaaaa aattttttcc    8460
tatttatata gaatcggaaa aaaaagagct ttttggaga  aatttaaata tagataaaaa    8520
acctattgtt cttatgatag caagagcttt atggcataaa ggtgtaaaag aattttatga    8580
aagtgctact atgctaaaag acaaagcaaa ttttgtttta gttggtggaa gagatgaaaa    8640
tccttcttgt gcgagtttgg agttttaaa  ctcgggtgtg gtgcattatt tgggtgctag    8700
aagtgatata gtcgagcttt tgcaaaattg tgatatttt  gttttaccaa gctataaaga    8760
aggctttcct gtaagtgttt tggaggcaaa agcttgtggc aaggctatag tggtgagtga    8820
ttgtgaaggt tgtgtagagg ctatttctaa tgcttatgat ggactttggg caaaaacaaa    8880
aaatgctaag gatttaagcg aaaaaatttc acttttatta aagatgaaa  aattaagatt    8940 aaatttagct aaaaatgctg cccaagatgc tttacaatac gatgaaaata atatcgcaca    9000
gcgttattta aaactttatg ataggtaat  taagaatgta tgaaaaagtt tttaaaagaa    9060
tttttgattt tattttagct ttagtgcttt tagtactttt ttctccggtg attttaatca    9120
ctgctttact tttaaaaatc actcaaggaa gtgtgatttt cactcaaaat cgccctgggt    9180
tagatgaaaa aattttaaa  atttataaat ttaaaaccat gagcgatgaa agagatgaga    9240
agggtgagtt attaagcgat gaattgcgtt tgaaagcctt tggaaaaatt gttagaagct    9300
taagtttgga tgagcttttg caacttttta atgttttaaa aggggatatg agttttgtgg    9360
ggcctagacc tcttttggtt gagtatttat ccctttataa tgaagagcaa aaattgcgcc    9420
ataaggtgcg tccaggtata acaggatggg cgcaggtaaa tggcagaaat gctatttctt    9480
ggcagaaaaa attcgaactt gatgtgtatt atgtgaaaaa tatttctttt ttgcttgatt    9540
taaaaatcat gttttaaca  gctttaaagg ttttaaaacg aagcgggta  agcaaagaag    9600 gccatgttac aacagagaaa tttaatggca agaactgaaa aaatttatat ttatggtgct    9660
agtggtcatg ggcttgtttg tgaagatgtg gctaaaaata tgggctataa agaatgtatt    9720 ttttagatg  attttaaagg aatgaaattt gaaacaccct tgcctaaata tgattttttt    9780
atagctatag gaaacaatga aattcgaaaa aagatttatc aaaaaatttc agaaatggc    9840 tttaaaatag ttaatcttat tcataaaagt gcacttataa gtcctagtgc aagcgtggaa    9900
gaaaatgcag ggattttaat tatgccctat gtagtgatta acgctaaagc caaaatagaa    9960
aaaggcgtga ttttaaatac ttcaagtgtg attgagcatg aatgcgtgat agggaattt   10020 tctcatgtaa gcgtagggc  taaatgtgcg ggtaatgtaa aaatcggtaa aaattgttt   10080 ttagggatta attcttgtgt tttgcctaat ttaagcttag cagatgatag tattttgggt   10140 ggtgagcaa  ctttggttaa aagccaaaat gaaaaaggtg tttttgtggg agtgcctgca   10200
aaaagaaaaa tatgaaatga ttataaaaag attttgttt  gattctttgt aaatttttt   10260
```

```
aggtaaaata gagttaattt ataaaaattt tgttttatac aaaggataaa tcatgagatt    10320
ttttctttct cctccgcata tgggcggtaa tgaattaaaa tatatagaag aagttttcaa    10380
aagcaattat atagcacctt tgggtgaatt tgtaaatcgc tttgagcaaa gtgtaaaaga    10440
ttatagcaaa agtgaaaatg ccttagcttt aaattcagct acagcagctt tgcatttagc    10500
tttaagggtg gcaggggtaa aacaagatga tattgttttg gcttcttctt ttacttttat    10560
cgcttcagtg gcgcctattt gttatcttaa agcaaaacct gtatttatag attgtgatga    10620
aacttataat atcgatgtag atttgttaaa acttgctatt aaggaatgtg aaaaaaaacc    10680
aaaagcattg attttaactc atctttatgg caatgcggct aaaatggatg aaattgttga    10740
aatttgcaag gaaaatgaaa ttgttttaat cgaagatgct gctgaagctt taggaagttt    10800
ttataagaat aaagccttag gaacttttgg agaatttgga gctattcttc taatggcaa    10860 taaaattatc accacttcag gtggaggtat gcttatagga aaaataaag aaaagattga    10920 aaaagcaaga ttttatagca ctcaagctag ggaaaattgt ttgcattatg aacatttaga    10980
ctatggttat aattaccgtt taagcaatgt tttaggagct attggtgtag cacaaatgga    11040
ggttttagaa caaagagtgc ttaaaaaaag agaaatttat gagtggtata aagaattttt    11100
aggagagtat tttagctttt tagatgaatt agaaaattca agaagtaatc gctggttaag    11160
tacagctttg attgattttg ataaaaatga acttaatgct tgtcaaaaag atataaatat    11220
cagtcaaaaa aatattactt tgcatccaaa aatttcaaaa ctcatagaag atttgaaaaa    11280
tgaacaaata gaaacaagac cattatggaa agctatgcac actcaagaag tatttaaagg    11340
aactaaggct tatcttaatg gcaatagtga gttattttc caaaaggaa tttgtttgcc    11400 aagtggtacg gcgatgagca aagatgatgt ttatgaaatt tcaaaactga tcttaaagag    11460
cataaaggct taaaatgatt ttttataaaa gcaaagatt agcattttt ttaacttcag    11520 atattgtttt aattttactt agtgtttatc tggcttttc tttgagattt agtggagata    11580
ttccgagtat ttttttatcat ggcatgatgg tttctgctat tattttgctt gttttaaaac    11640
tttcattttt gtttgttttt agaatttata aagtagcttg gagatttttt tccctcaatg    11700
aagcaagaaa aatttttatc gctttgcttt tagctgagtt ttgttttttt cttattttt    11760 atttttttag tgattttttt aatccttttc caagaagtgc tattgtgata gattttgttc    11820
tttcttatat gtttataggt actttaagaa ttagcaaaag aatgcttgtg gatttaaac    11880 cttctaaaat gaaagaagaa gaaactcctt gtattgtagt aggggcaact tctaaggctt    11940
tacatttgtt aaaaggcgca aaagaaggtt ctttagggct ttttcctgtg ggcgtagttg    12000
atgcgagaaa agagcttata gggacttatt gtgataaatt tgttgtagaa gaaaagaaa    12060 aaataaaatc ttatgtagaa caaggggtaa aaactgccat tattgcttta agacttgaac    12120
aagaagagct taaaaaactt tttgaagaac ttgtagctta tggtatttgt gatgtaaaaa    12180
tattttcttt tacaagaaat gaagcaagag atattagtat agaagacttg cttgctagaa    12240
aaccaaaaga tttagacgat agtgctgtgg cggcttttt aaaagacaag gtagttttgg    12300
taagtggagc aggtggaact ataggcagtg aactttgtaa gcaatgtatt aaatttggtg    12360
ctaagcatct tattatggtt gatcatagtg agtataatct ttataagatc aatgatgatt    12420
taaatttata taagaaaaa attactccta ttttgttaag tattttagat aagcaaagtt    12480
tagatgaggt attaaaaact tataaacctg agcttatttt acatgcagcc gcttataaac    12540
atgtgcctct ttgcgaacaa aatccacatt cagcagtaat caataatatt ttaggaacca    12600
```

```
aaatttttatg cgacagtgct aaagaaaata aagtagctaa atttgtgatg ataagtacag    12660
ataaagcagt acgaccaaca aatattatgg gttgcactaa gagagtttgt gagctttata    12720
ctttaagtat gagtgatgaa aattttgaag ttgcttgtgt gcgttttggt aatgttttag    12780
gttctagtgg tagtgtgata ccgaaattta aagcacaaat tgccaataat gagcctttaa    12840
ctttaacaca ccctgatata gtgcgttatt ttatgcttgt ggctgaggca gtgcaacttg    12900
ttttgcaagc tggagctatc gcaaaagggg agaactttt tgttttggat atgggtaagc    12960
ctgtgaaaat catagattta gctaaaaaaa tgcttttact ttctaatcgc aatgatttag    13020
aaattaaaat cacaggttta agaaaaggtg agaagcttta tgaagagctt ttgattgatg    13080
aaaatgatgc taaaacccaa tatgagagta tttttgtagc aaagaatgag aaggttgatc    13140
ttgattggct taataaagag atagaaaatt tacaaatatg tgaagatatt tcagaggctt    13200
tattaaagat tgtacctgaa tttaaacaca ataagaagg catataatgt atataaaaga    13260
tatacaaaga tttgaagata atcgctatcg tgctagagct tatatgagtt atattttaac    13320
aagaaatcta cccaataaac ttcctgatat tcaccttgaa acgattaaaa cagctttgga    13380
taaaatagct catgaagttg ttgttttga tgctttgtat attttagata tttcaggcat    13440
gcaaatagaa aatgcgattt ccttaaataa ggctcatgaa atagggcagg gtgaggatag    13500
aagtactcgt tcttattttt atagagctgt aaaattaaaa cgatgtgttt tgagcgatcc    13560
ttatccttcg gttttaaaca atgaactttg cgtaacagct tctataccaa tttacgatga    13620
taaaaataac ttgcttttg ttgtttgtat tgatatcaag cttgaagata ttttaaagat    13680
tattcaagca ggaaaatttg agtttgtttt tactcaattt agtcgtttgg tgtatttttg    13740
tttcgcactg gttttatttg tgattacttg ttttttattt caaaaggtt tttttagtct    13800 ttttgataat caagctatag gcatagaaca tatgtttgaa agtaccattg ccataactttt    13860 agctttagct attttttgatt tggcaaaaac tttgatcgaa caagaagtat taggaaggac    13920
aaaaaaagaa gaaggtggaa ttcaaaaaac catggtgaga ttttgggtt ctattatcat    13980 tgctttagct atagaagctt tgatgttggt atttaaactt gctattggtg atctttctca    14040
gatgatttat gcgatttatc ttatcggtgg agtgagcttg cttcttttag gcttaagtgt    14100
atatttattt acggttaagt ataaaaataa taatatttga gtaaaaattt aagtaaaaga    14160
tgatataatg ctgtttttta aaattttta gcttgattaa taaggctaaa aagggtaaaa    14220
taaaactata aaaactttga aaggacgaaa ttgtgaaatt gttagttgtt gatgacagtt    14280
ctactatgag aaggattatt aaaaataccc taacaagact tggacacgat gatgtttag    14340 aagctgagca tggcgttgaa gcttgggatt tattaactaa aaatgaagat gtaaagtttt    14400
taattacaga ttggaatatg ccagaaatga atggcttgga gttggtaaaa aagtaagag    14460 cagagaaaaa atatgaagat atgcctatta tcatggttac aactgagggc ggaaaagctg    14520
aagtgattac tgcttaaaaa gctggcgtaa ataactatat tgtaaaacct tttactccac    14580
aagttttaaa ggaaaaactt gaagatgttt taggaacagg aagtggagaa ggtgcagctg    14640
agtaa                                                                14645
```

<210> SEQ ID NO 13
<211> LENGTH: 31
<212> TYPE: DNA
<213> ORGANISM: artificial sequence
<220> FEATURE:
<223> OTHER INFORMATION: primer

<400> SEQUENCE: 13
ttttgcggcc gcttctacgt gttccgcttc c                               31

<210> SEQ ID NO 14
<211> LENGTH: 31
<212> TYPE: DNA
<213> ORGANISM: artificial sequence
<220> FEATURE:
<223> OTHER INFORMATION: primer

<400> SEQUENCE: 14
ttttgcggcc gcattgcgtt gcgctcactg c                               31

<210> SEQ ID NO 15
<211> LENGTH: 603
<212> TYPE: DNA
<213> ORGANISM: artificial sequence
<220> FEATURE:
<223> OTHER INFORMATION: transposon

<400> SEQUENCE: 15
ggccgcctag gccgcggccg cctacttcgt atagcataca ttatacgaag ttatgtctga     60
cgctcagtgg aacgacgcgt aactcacgtt aagggatttt ggtcatgatc agcacgttga    120
caattaatca tcggcatagt atatcggcat agtataatac gacaaggtga ggaactaaaa    180
catggccaag ttgaccagtg ccgttccggt gctcaccgcg cgcgacgtcg ccggagcggt    240
cgagttctgg accgaccggc tcgggttctc ccgggacttc gtggaggacg acttcgccgg    300
tgtggtccgg gacgacgtga ccctgttcat cagcgcggtc caggaccagg tggtgccgga    360
caacaccctg gcctgggtgt gggtgcgcgg cctggacgag ctgtacgccg agtggtcgga    420
ggtcgtgtcc acgaacttcc gggacgcctc cgggccggcc atgaccgaga tcggcgagca    480
gccgtggggg cgggagttcg ccctgcgcga cccggccggc aactgcgtgc acttcgtggc    540
cgaggagcag gactgaataa cttcgtatag catacattat acgaagttat ggccgcctag    600
gcc                                                                  603

<210> SEQ ID NO 16
<211> LENGTH: 47
<212> TYPE: DNA
<213> ORGANISM: artificial sequence
<220> FEATURE:
<223> OTHER INFORMATION: primer

<400> SEQUENCE: 16
ttttgaattc gattatcgcc atggcgtcaa attttaattt cgctaaa                   47

<210> SEQ ID NO 17
<211> LENGTH: 41
<212> TYPE: DNA
<213> ORGANISM: artificial sequence
<220> FEATURE:
<223> OTHER INFORMATION: primer

<400> SEQUENCE: 17
ttttgaattc ttattttttg agtttataaa ttttagttga t                        41

<210> SEQ ID NO 18
<211> LENGTH: 19
<212> TYPE: DNA
<213> ORGANISM: artificial sequence
<220> FEATURE:
<223> OTHER INFORMATION: primer

```
<400> SEQUENCE: 18
gcgctggctg gtttagttt                                                    19

<210> SEQ ID NO 19
<211> LENGTH: 18
<212> TYPE: DNA
<213> ORGANISM: artificial sequence
<220> FEATURE:
<223> OTHER INFORMATION: primer

<400> SEQUENCE: 19
cgcattcgtt ccagaggt                                                     18

<210> SEQ ID NO 20
<211> LENGTH: 20
<212> TYPE: DNA
<213> ORGANISM: artificial sequence
<220> FEATURE:
<223> OTHER INFORMATION: primer

<400> SEQUENCE: 20
gacaaggaac aggcgatcag                                                   20

<210> SEQ ID NO 21
<211> LENGTH: 20
<212> TYPE: DNA
<213> ORGANISM: artificial sequence
<220> FEATURE:
<223> OTHER INFORMATION: primer

<400> SEQUENCE: 21
tggtgatgat ggtgatggtc                                                   20

<210> SEQ ID NO 22
<211> LENGTH: 37
<212> TYPE: DNA
<213> ORGANISM: artificial sequence
<220> FEATURE:
<223> OTHER INFORMATION: primer

<400> SEQUENCE: 22
aagaattcat gttgaaaaaa gagtatttaa aaaaccc                                37

<210> SEQ ID NO 23
<211> LENGTH: 62
<212> TYPE: DNA
<213> ORGANISM: artificial sequence
<220> FEATURE:
<223> OTHER INFORMATION: primer

<400> SEQUENCE: 23
aaccatggtt aagcgtaatc tggaacatcg tatgggtaaa ttttaagttt aaaaaccttta     60 gc                                                                     62

<210> SEQ ID NO 24
<211> LENGTH: 43
<212> TYPE: DNA
<213> ORGANISM: artificial sequence
<220> FEATURE:
<223> OTHER INFORMATION: Primer

<400> SEQUENCE: 24
ttacttactt ccctctctca atatttcaat attcatagct cct                        43
```

```
<210> SEQ ID NO 25
<211> LENGTH: 43
<212> TYPE: DNA
<213> ORGANISM: artificial sequence
<220> FEATURE:
<223> OTHER INFORMATION: Primer

<400> SEQUENCE: 25
aggagctatg aatattgaaa tattgagaga gggaagtaag taa          43

<210> SEQ ID NO 26
<211> LENGTH: 34
<212> TYPE: DNA
<213> ORGANISM: artificial sequence
<220> FEATURE:
<223> OTHER INFORMATION: Primer

<400> SEQUENCE: 26
tatattgaat tcaattacaa agattacagg tttg                    34

<210> SEQ ID NO 27
<211> LENGTH: 34
<212> TYPE: DNA
<213> ORGANISM: artificial sequence
<220> FEATURE:
<223> OTHER INFORMATION: Primer

<400> SEQUENCE: 27
agttcaggat cctcctttaa acaacttctc atac                    34

<210> SEQ ID NO 28
<211> LENGTH: 20
<212> TYPE: DNA
<213> ORGANISM: artificial sequence
<220> FEATURE:
<223> OTHER INFORMATION: Primer

<400> SEQUENCE: 28
ctgcggctag tctcgctatt                                    20

<210> SEQ ID NO 29
<211> LENGTH: 20
<212> TYPE: DNA
<213> ORGANISM: artificial sequence
<220> FEATURE:
<223> OTHER INFORMATION: Primer

<400> SEQUENCE: 29
catgcgcttc aaattcattc                                    20

<210> SEQ ID NO 30
<211> LENGTH: 32
<212> TYPE: DNA
<213> ORGANISM: artificial sequence
<220> FEATURE:
<223> OTHER INFORMATION: Primer

<400> SEQUENCE: 30
agttcacata tgcgggtggt atcggtacac tt                      32

<210> SEQ ID NO 31
<211> LENGTH: 48
<212> TYPE: DNA
<213> ORGANISM: artificial sequence
<220> FEATURE:
<223> OTHER INFORMATION: Primer
```

<400> SEQUENCE: 31
cctttttgtt aataagaaaa tcagtttctg tatcataatc cgaacttc          48

<210> SEQ ID NO 32
<211> LENGTH: 48
<212> TYPE: DNA
<213> ORGANISM: artificial sequence
<220> FEATURE:
<223> OTHER INFORMATION: Primer

<400> SEQUENCE: 32
gaagttcgga ttatgataca gaaactgatt ttcttattaa caaaaagg          48

<210> SEQ ID NO 33
<211> LENGTH: 32
<212> TYPE: DNA
<213> ORGANISM: artificial sequence
<220> FEATURE:
<223> OTHER INFORMATION: Primer

<400> SEQUENCE: 33
ttcgtatgga tccaactacg gtgaccggca at          32

<210> SEQ ID NO 34
<211> LENGTH: 20
<212> TYPE: DNA
<213> ORGANISM: artificial sequence
<220> FEATURE:
<223> OTHER INFORMATION: Primer

<400> SEQUENCE: 34
gagaattgaa ggaagtgata          20

<210> SEQ ID NO 35
<211> LENGTH: 20
<212> TYPE: DNA
<213> ORGANISM: artificial sequence
<220> FEATURE:
<223> OTHER INFORMATION: Primer

<400> SEQUENCE: 35
atataaggag tacaggttag          20

<210> SEQ ID NO 36
<211> LENGTH: 32
<212> TYPE: DNA
<213> ORGANISM: artificial sequence
<220> FEATURE:
<223> OTHER INFORMATION: Primer

<400> SEQUENCE: 36
agttcagcta gcgggcaaag aatttcggta ca          32

<210> SEQ ID NO 37
<211> LENGTH: 42
<212> TYPE: DNA
<213> ORGANISM: artificial sequence
<220> FEATURE:
<223> OTHER INFORMATION: Primer

<400> SEQUENCE: 37
ctttctgagg ttccatggta aggagccatt tgatcatgaa at          42

<210> SEQ ID NO 38
<211> LENGTH: 42

```
<212> TYPE: DNA
<213> ORGANISM: artificial sequence
<220> FEATURE:
<223> OTHER INFORMATION: Primer

<400> SEQUENCE: 38
atttcatgat caaatggctc cttaccatgg aacctcagaa ag                           42

<210> SEQ ID NO 39
<211> LENGTH: 35
<212> TYPE: DNA
<213> ORGANISM: artificial sequence
<220> FEATURE:
<223> OTHER INFORMATION: Primer

<400> SEQUENCE: 39
ttcgtatgga tccgtagtcc aaatgagcta cttac                                  35

<210> SEQ ID NO 40
<211> LENGTH: 20
<212> TYPE: DNA
<213> ORGANISM: artificial sequence
<220> FEATURE:
<223> OTHER INFORMATION: Primer

<400> SEQUENCE: 40
gacaagccaa ctgaaacaac                                                   20

<210> SEQ ID NO 41
<211> LENGTH: 20
<212> TYPE: DNA
<213> ORGANISM: artificial sequence
<220> FEATURE:
<223> OTHER INFORMATION: Primer

<400> SEQUENCE: 41
agattcccct gatttagcta                                                   20

<210> SEQ ID NO 42
<211> LENGTH: 18
<212> TYPE: DNA
<213> ORGANISM: artificial sequence
<220> FEATURE:
<223> OTHER INFORMATION: Primer

<400> SEQUENCE: 42
actggccgtc gttttaca                                                     18

<210> SEQ ID NO 43
<211> LENGTH: 18
<212> TYPE: DNA
<213> ORGANISM: artificial sequence
<220> FEATURE:
<223> OTHER INFORMATION: Primer

<400> SEQUENCE: 43
caggaaacag ctatgacc                                                     18

<210> SEQ ID NO 44
<211> LENGTH: 5
<212> TYPE: PRT
<213> ORGANISM: artificial sequence
<220> FEATURE:
<223> OTHER INFORMATION: glycosylation motif

<400> SEQUENCE: 44
```

Asp Gln Asn Ala Thr
1               5

<210> SEQ ID NO 45
<211> LENGTH: 5
<212> TYPE: PRT
<213> ORGANISM: artificial sequence
<220> FEATURE:
<223> OTHER INFORMATION: glycosylation motif

<400> SEQUENCE: 45

Asp Asn Asn Asn Thr
1               5

<210> SEQ ID NO 46
<211> LENGTH: 5
<212> TYPE: PRT
<213> ORGANISM: artificial sequence
<220> FEATURE:
<223> OTHER INFORMATION: glycosylation motif

<400> SEQUENCE: 46

Asp Asn Asn Asn Ser
1               5

<210> SEQ ID NO 47
<211> LENGTH: 5
<212> TYPE: PRT
<213> ORGANISM: artificial sequence
<220> FEATURE:
<223> OTHER INFORMATION: glycosylation motif

<400> SEQUENCE: 47

Asp Gln Asn Arg Thr
1               5

<210> SEQ ID NO 48
<211> LENGTH: 5
<212> TYPE: PRT
<213> ORGANISM: artificial sequence
<220> FEATURE:
<223> OTHER INFORMATION: glycosylation motif

<400> SEQUENCE: 48

Glu Asn Asn Phe Thr
1               5

<210> SEQ ID NO 49
<211> LENGTH: 5
<212> TYPE: PRT
<213> ORGANISM: artificial sequence
<220> FEATURE:
<223> OTHER INFORMATION: glycosylation motif

<400> SEQUENCE: 49

Asp Ser Asn Ser Thr
1               5

<210> SEQ ID NO 50
<211> LENGTH: 5
<212> TYPE: PRT
<213> ORGANISM: artificial sequence
<220> FEATURE:
<223> OTHER INFORMATION: glycosylation motif

<400> SEQUENCE: 50

Asp Gln Asn Ile Ser 1               5

<210> SEQ ID NO 51
<211> LENGTH: 5
<212> TYPE: PRT
<213> ORGANISM: artificial sequence
<220> FEATURE:
<223> OTHER INFORMATION: glycosylation motif

<400> SEQUENCE: 51

Asp Gln Asn Val Ser
1               5

<210> SEQ ID NO 52
<211> LENGTH: 5
<212> TYPE: PRT
<213> ORGANISM: artificial sequence
<220> FEATURE:
<223> OTHER INFORMATION: glycosylation motif

<400> SEQUENCE: 52

Asp Asn Asn Val Ser
1               5

<210> SEQ ID NO 53
<211> LENGTH: 5
<212> TYPE: PRT
<213> ORGANISM: artificial sequence
<220> FEATURE:
<223> OTHER INFORMATION: glycosylation motif

<400> SEQUENCE: 53

Asp Tyr Asn Val Ser
1               5

<210> SEQ ID NO 54
<211> LENGTH: 5
<212> TYPE: PRT
<213> ORGANISM: artificial sequence
<220> FEATURE:
<223> OTHER INFORMATION: glycosylation motif

<400> SEQUENCE: 54

Asp Phe Asn Val Ser
1               5

<210> SEQ ID NO 55
<211> LENGTH: 5
<212> TYPE: PRT
<213> ORGANISM: artificial sequence
<220> FEATURE:
<223> OTHER INFORMATION: glycosylation motif

<400> SEQUENCE: 55

Asp Phe Asn Ala Ser
1               5

<210> SEQ ID NO 56
<211> LENGTH: 5
<212> TYPE: PRT
<213> ORGANISM: artificial sequence
<220> FEATURE:
<223> OTHER INFORMATION: glycosylation motif

<400> SEQUENCE: 56

Asp Phe Asn Ser Ser
1               5

<210> SEQ ID NO 57
<211> LENGTH: 5
<212> TYPE: PRT
<213> ORGANISM: artificial sequence
<220> FEATURE:
<223> OTHER INFORMATION: glycosylation motif

<400> SEQUENCE: 57

Asp Val Asn Ala Thr
1               5

<210> SEQ ID NO 58
<211> LENGTH: 5
<212> TYPE: PRT
<213> ORGANISM: artificial sequence
<220> FEATURE:
<223> OTHER INFORMATION: glycosylation motif

<400> SEQUENCE: 58

Asp Phe Asn Val Thr
1               5

<210> SEQ ID NO 59
<211> LENGTH: 5
<212> TYPE: PRT
<213> ORGANISM: artificial sequence
<220> FEATURE:
<223> OTHER INFORMATION: glycosylation motif

<400> SEQUENCE: 59

Asp Val Asn Ala Ser
1               5

<210> SEQ ID NO 60
<211> LENGTH: 5
<212> TYPE: PRT
<213> ORGANISM: artificial sequence
<220> FEATURE:
<223> OTHER INFORMATION: glycosylation motif

<400> SEQUENCE: 60

Asp Val Asn Val Thr
1               5

<210> SEQ ID NO 61
<211> LENGTH: 5
<212> TYPE: PRT
<213> ORGANISM: artificial sequence
<220> FEATURE:
<223> OTHER INFORMATION: glycosylation motif

<400> SEQUENCE: 61

Glu Val Asn Ala Thr
1               5

<210> SEQ ID NO 62
<211> LENGTH: 5
<212> TYPE: PRT
<213> ORGANISM: Artificial Sequence
<220> FEATURE:
<223> OTHER INFORMATION: synthetic peptide sequence
<220> FEATURE:
<221> NAME/KEY: MISC_FEATURE
<222> LOCATION: (1)..(1)
<223> OTHER INFORMATION: X is Aspartic acid or glutamic acid
<220> FEATURE:
<221> NAME/KEY: MISC_FEATURE

```
<222> LOCATION: (2)..(2)
<223> OTHER INFORMATION: X is any amino acid except proline
<220> FEATURE:
<221> NAME/KEY: MISC_FEATURE
<222> LOCATION: (4)..(4)
<223> OTHER INFORMATION: X is any amino acid except proline
<220> FEATURE:
<221> NAME/KEY: MISC_FEATURE
<222> LOCATION: (5)..(5)
<223> OTHER INFORMATION: X is serine or threonine

<400> SEQUENCE: 62

Xaa Xaa Asn Xaa Xaa
1               5

<210> SEQ ID NO 63
<211> LENGTH: 50
<212> TYPE: DNA
<213> ORGANISM: Artificial sequence
<220> FEATURE:
<223> OTHER INFORMATION: Vector and C. sputorum pglB sequence

<400> SEQUENCE: 63
atttcacaca ggaaacagaa ttcatggcgt caaattttaa tttcgctaaa               50

<210> SEQ ID NO 64
<211> LENGTH: 27
<212> TYPE: DNA
<213> ORGANISM: Campylobacter sputorum

<400> SEQUENCE: 64
atggcgtcaa attttaattt cgctaaa                                        27

<210> SEQ ID NO 65
<211> LENGTH: 60
<212> TYPE: DNA
<213> ORGANISM: Artificial Sequence
<220> FEATURE:
<223> OTHER INFORMATION: Vector and C. sputorum pglB sequence

<400> SEQUENCE: 65
atttcacaca ggaaacagaa ttcgattatc gccatggcgt caaattttaa tttcgctaaa    60
```